United States Patent [19]

Heckmann et al.

[11] Patent Number: 5,856,509

[45] Date of Patent: *Jan. 5, 1999

[54] DERIVATIVES OF IMIDAZOLE, THEIR PREPARATION PROCESS, THE NEW INTERMEDIATES OBTAINED, THEIR USE AS MEDICAMENTS AND THE PHARMACEUTICAL COMPOSITIONS CONTAINING THEM

[75] Inventors: Bertrand Heckmann, Cachan; Jean-Paul Vevert, Pantin; Jidong Zhang, Paris, all of France

[73] Assignee: Roussel Uclaf, France

[ * ] Notice: The term of this patent shall not extend beyond the expiration date of Pat. No. 5,811,444.

[21] Appl. No.: 776,954

[22] PCT Filed: Aug. 1, 1995

[86] PCT No.: PCT/FR95/01033

§ 371 Date: Jan. 31, 1997

§ 102(e) Date: Jan. 31, 1997

[87] PCT Pub. No.: WO96/04275

PCT Pub. Date: Feb. 15, 1996

[30] Foreign Application Priority Data

Aug. 2, 1994 [FR] France .................................. 94/09565

[51] Int. Cl.$^6$ ..................... C07D 233/54; C07D 403/14; C07D 31/415; A01K 00/00
[52] U.S. Cl. ......................................... 548/311.1; 514/387
[58] Field of Search .......................... 548/311.7; 514/397

[56] References Cited

FOREIGN PATENT DOCUMENTS 2416012  1/1979  France .
94/02474  2/1994  WIPO .

OTHER PUBLICATIONS

Chem Abstracts. Oct. 14, 1995, vol. 103, No. 15,C. Paul Bianchi #115 118v. Journal of Med. Chemistry, 1975, vol. 18, No. 8, 4 pgs. 833–836, Baggalby et al.

S. Farmaco, Edizione Scientifica, vol. 40, pp. 429–441 (1985) Stefancich et al.

*Primary Examiner*—Floyd D. Higel
*Attorney, Agent, or Firm*—Bierman, Muserlian and Lucas

[57] ABSTRACT

The invention relates to the products of formula (I):

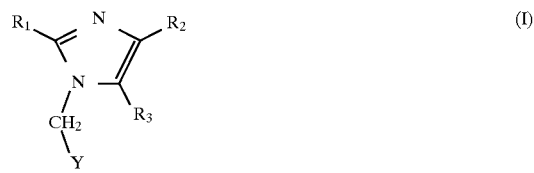

in which:

$R_1$=represents hydrogen, aryl, arylcarbonyl, arylthio, alkylcarbonyl, $R_2$, $R_3$ represent in particular halogen, mercapto, acyl, carboxy, nitro, cyano, amino, carbamoyl, $R_4$, —$OR_4$ with $R_4$ representing in particular hydrogen, alkyl, alkenyl, alkynyl, acyl, amino, —$(CH_2)_{m1}$—$S(O)_{m2}$—X—$R_{10}$ with m1=0 to 4, m2=0 to 2, X represents a single bond or —NH—, —NH—CO—, —NH—CO—NH—, and $R_{10}$ represents alkyl, alkenyl or aryl, and Y represents optionally substituted aryl, these products being in all isomer forms and salts, their use as medicaments.

10 Claims, No Drawings

DERIVATIVES OF IMIDAZOLE, THEIR PREPARATION PROCESS, THE NEW INTERMEDIATES OBTAINED, THEIR USE AS MEDICAMENTS AND THE PHARMACEUTICAL COMPOSITIONS CONTAINING THEM

This application is a 371 of PCT/FR95/01033 filed Aug. 1, 1995.

The present invention relates to new derivatives of imidazole, their preparation process, the new intermediaries obtained, their use as medicaments and the pharmaceutical compositions containing them.

A subject of the invention is the products of formula (I):

in which:

$R_1$ represents a hydrogen atom, a hydroxyl, alkoxyl, formyl, dioxol, an aryl, arylcarbonyl, arylthio, alkylcarbonyl radical in which the alkyl radical is linear or branched, containing at most 6 carbon atoms, the aryl and alkyl radicals in all the radicals which can be represented by $R_1$ being optionally substituted by one or more identical or different radicals chosen from halogen atoms, the following radicals: hydroxyl, free, salified, esterified or amidified carboxy, cyano, nitro, amino optionally substituted by one or two identical or different alkyl radicals containing at most 6 carbon atoms, cycloalkyl containing 3 to 7 carbon atoms, alkyl, alkenyl and alkoxy containing at most 6 carbon atoms, haloalkyl, alkylthio, haloalkylthio, haloalkoxy, phenoxy, phenylalkoxy, optionally substituted carbamoyl, acyl, acyloxy, optionally salified tetrazolyl and phenyl optionally substituted by one or more radicals chosen from halogen atoms, hydroxyl radicals, alkyl and alkoxy radicals containing at most 4 carbon atoms, trifluoromethyl, cyano, free, salified or esterified carboxy and tetrazolyl radicals, $R_2$ and $R_3$, identical or different, are chosen from:

a) halogen atoms, mercapto, acyl, free, salified, esterified or amidified carboxy, nitro, cyano radicals, and the —P(O)(OR)$_2$ radical in which R represents a hydrogen atom, an alkyl or phenyl radical, b) the $R_4$ and —OR$_4$ radicals in which:

either $R_4$ represents the —(CH$_2$)$_{m1}$—S(O)$_{m2}$—X—R$_{10}$ radical in which m1 represents an integer from 0 to 4, m2 represents an integer from 0 to 2 and either X—R$_{10}$ represents an amino radical or X represents a single bond or the —NR$_{11}$—, —NR$_{11}$—CO—, —NR$_{11}$—CO—O—, —NR$_{11}$—CO—NR$_{12}$— and —N=CR$_{11}$—NR$_{12}$— radicals and R$_{10}$ represents an alkyl, alkenyl or aryl radical these radicals being optionally substituted by one or more identical or different radicals chosen from halogen atoms, hydroxyl radicals, cycloalkyl radicals containing 3 to 7 carbon atoms, alkyl, alkoxy, haloalkyl, alkylthio, haloalkylthio and haloalkoxy radicals, linear or branched, containing at most 6 carbon atoms, phenoxy, phenylalkoxy, optionally substituted carbamoyl, acyl, acyloxy, free, salified or esterified carboxy, tetrazolyl, cyano, nitro radicals, amino radicals optionally substituted by one or two identical or different alkyl radicals containing at most 6 carbon atoms and aryl radicals optionally substituted by one or more radicals chosen from halogen atoms, hydroxyl radicals, alkyl and alkoxy radicals containing at most 4 carbon atoms, trifluoromethyl, free, salified or esterified carboxy and tetrazolyl radicals, and $R_{11}$ and $R_{12}$, identical or different, are chosen from the hydrogen atom and the values defined for $R_{10}$, or $R_4$ represents the hydrogen atom; an alkyl, alkenyl, alkynyl and acyl radical, these radicals being linear or branched, containing at most 6 carbon atoms, and being optionally interrupted by one or more heteroatoms chosen from sulphur, oxygen or nitrogen atoms; an amino or carbamoyl radical optionally substituted by one or two identical or different alkyl or alkenyl radicals containing at most 6 carbon atoms or the (CH$_2$)$_{m1}$—S(O)$_{m2}$—XR$_{10}$ radical as defined above; a cycloalkyl radical containing 3 to 6 carbon atoms or an aryl radical, the alkyl, alkenyl and aryl radicals of all the radicals which are represented by $R_4$ being optionally substituted by one or more identical or different radicals chosen from:

halogen atoms, hydroxyl, mercapto, cyano, azido, nitro radicals,

SO$_3$H, free, salified, esterified or amidified carboxy radicals, alkyl, alkenyl, alkoxy, haloalkyl, alkylthio, alkenylthio, alkynylthio, acyl, acyloxy, acylthio, haloalkylthio, haloalkoxy radicals, these radicals containing at most 6 carbon atoms, aryl, arylalkyl, arylalkenyl, arylthio, aryloxy and arylalkoxy radicals in which the aryl radical is optionally substituted by one or more identical or different radicals chosen from halogen atoms, hydroxyl radicals, alkyl and alkoxy radicals containing at most 6 carbon atoms, haloalkyl, alkylthio, haloalkylthio, haloalkoxy radicals, optionally substituted carbamoyl, acyl, acyloxy, free, salified or esterified carboxy, cyano, nitro radicals, amino radicals optionally substituted by one or two identical or different alkyl radicals containing at most 6 carbon atoms, tetrazolyl and phenyl radicals optionally substituted by one or more radicals chosen from halogen atoms, hydroxyl radicals, alkyl and alkoxy radicals containing at most 4 carbon atoms, trifluoromethyl, free, salified or esterified carboxy and tetrazolyl radicals, and the

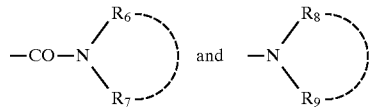

radicals in which:

either $R_6$ and $R_7$ or $R_8$ and $R_9$, identical or different, are chosen from:

the hydrogen atom, amino acids, alkyl and alkenyl radicals containing at most 6 carbon atoms and optionally substituted by one or more identical or different radicals chosen from halogen atoms, the hydroxyl radical or alkoxy radicals containing at most 6 carbon atoms, aryl, arylalkyl and arylalkenyl radicals in which the linear or branched alkyl and alkenyl radicals contain at most 6 carbon atoms, these aryl, arylalkyl and arylalkenyl radicals being optionally substituted by one or more radicals chosen from halogen atoms, hydroxyl, nitro, cyano radicals, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified or esterified carboxy radicals, aryl and arylalkyl radicals, these last two radicals being optionally substituted by one or more radicals chosen from halogen atoms, hydroxyl, trifluoromethyl, nitro, cyano, free, salified or esterified carboxy and tetrazolyl radicals, the —$(CH_2)_{m1}$—$S(O)_{m2}$—X—$R_{10}$ radical as defined above, or $R_6$ and $R_7$ or $R_8$ and $R_9$ form respectively with the nitrogen atom to which they are linked a monocyclic radical containing 5, 6 or 7 members or a radical constituted by condensed rings containing 8 to 14 members, these identical or different radicals optionally containing one or more other heteroatoms chosen from oxygen, nitrogen and sulphur atoms, and being optionally substituted by one or more radicals chosen from halogen atoms, hydroxyl, nitro, cyano radicals, alkyl, alkenyl, haloalkyl, alkoxy and acyl radicals, these radicals containing at most 6 carbon atoms, amino radicals optionally substituted by one or two identical or different alkyl radicals containing at most 6 carbon atoms, free, salified, esterified or amidified carboxy radicals, aryl and arylalkyl radicals, these last two radicals being optionally substituted by one or more radicals chosen from halogen atoms, hydroxyl, trifluoromethyl, nitro, cyano, free, salified or esterified carboxy and tetrazolyl radicals, or $R_8$ and $R_9$, identical or different, represent an acyl radical or one of $R_8$ or $R_9$ represents a carbamoyl, alkoxycarbonyl or benzyloxycarbonyl radical and the other is chosen from the values defined above for $R_8$ and $R_9$ or $R_8$ and $R_9$ form together with the nitrogen atom to which they are linked a phthalimido or succinimido radical, Y represents the —$Y_1$—B—$Y_2$ radical in which:
  $Y_1$ represents an aryl radical optionally substituted by one or more radicals chosen from the dioxol radicals and the radicals which can be represented by $R_2$ and $R_3$,
  B represents a single bond between $Y_1$ and $Y_2$, or one of the following divalent radicals: —CO—, —O—, —NH—CO—, —CO—NH— or —O—$(CH_2)_p$— with p representing the values 1, 2 or 3,
  $Y_2$ is defined as follows:
    either, whatever the value of B and $Y_2$ being identical to or different from $Y_1$, $Y_2$ is chosen from the values defined for $Y_1$,
    or, if B represents a single bond, $Y_2$ represents a hydrogen atom, a halogen atom, an alkoxy, cyano, free, salified, esterified or amidified carboxy or carboxycarbonyl radical, a tetrazolyl radical or a $(CH_2)_{m1}$—$S(O)_{m2}$—$XR_{10}$ radical as defined above, the said products of formula (I) being in all possible racemic, enantiomeric and diastereoisomeric isomer forms, as well as the addition salts with mineral and organic acids or with mineral and organic bases of said products of formula (I).

In the products of formula (I) and in what follows:

the term linear or branched alkyl radical preferably designates the following radicals: methyl, ethyl, propyl, isopropyl, butyl, isobutyl, sec-butyl and tert-butyl but can also represent a pentyl or hexyl radical and particularly isopentyl and isohexyl, the term linear or branched alkenyl radical preferably designates one of the following radicals: vinyl, allyl, 1-propenyl, butenyl and particularly 1-butenyl, or pentenyl, the term linear or branched alkynyl radical preferably designates an ethynyl, propargyl, butynyl or pentynyl radical.

Among the alkyl radicals interrupted by one or more heteroatoms, there can be mentioned for example the following radicals: methoxymethyl, methoxyethoxymethyl, propylthiopropyl, propyloxypropyl, propylthioethyl, methylthiomethyl, the term halogen atom preferably designates the chlorine atom, but can also represent a fluorine, bromine or iodine atom, the term linear or branched alkoxy radical preferably designates methoxy, ethoxy, propoxy or isopropoxy radicals, but can also represent a linear, secondary or tertiary butoxy radical, the term acyl radical preferably designates a radical having 1 to 6 carbon atoms such as for example the formyl, acetyl, propionyl, butyryl or benzoyl radical, but also the pentanoyl, hexanoyl, acryloyl, crotonoyl or carbamoyl radical, the term acyloxy radical designates for example a radical in which the acyl radical has the values indicated above and preferably designates a formyloxy, acetyloxy, propionyloxy, butyryloxy or benzoyloxy radical, the term cycloalkyl radical preferably designates cyclopropyl, cyclobutyl radicals and quite particularly cyclopentyl and cyclohexyl radicals, the term haloalkyl radical preferably designates the radicals in which the alkyl radical is as defined above and is substituted by one or more halogen atoms as defined above such as for example in bromoethyl, trifluoromethyl, trifluoroethyl or also pentafluoroethyl, the term haloalkoxy radical preferably designates the radicals in which the alkoxy radical is as defined above and is substituted by one or more halogen atoms as defined above such as for example in bromoethoxy, trifluoromethoxy, trifluoroethoxy or also pentafluoroethoxy, the term dioxol radical can designate either a carboxycyclic radical containing at most 6 carbon atoms and 2 oxygen atoms, for example the 1,3-dioxolan radical or the dioxane radical, or a carbocyclic ring containing 2 oxygen atoms linked to an arylic substituent for example the 1,3-benzodiooxolyl radical, the term aryl radical designates an unsaturated monocyclic radical, containing 5, 6 or 7 members or a radical constituted by condensed rings containing 8 to 14 members, carbocyclic or heterocyclic, it being understood that the heterocyclic radicals can contain one or more heteroatoms chosen from oxygen, nitrogen or sulphur atoms and that when these heterocyclic radicals contain more than one heteroatom, the heteroatoms of these heterocyclic radicals can be identical or different.

As examples of such an aryl radical, the following radicals can be mentioned: phenyl, naphthyl, thienyl such as 2-thienyl and 3-thienyl, furyl such as 2-furyl, pyridyl such as 2-pyridyl and 3-pyridyl, pyrimidinyl, pyrrolyl, thiazolyl, isothiazolyl, pyrazolyl, triazolyl, tetrazolyl, salified tetrazolyl, diazolyl, thiadiazolyl, thiatriazolyl, oxazolyl, oxadiazolyl, 3- or 4-isoxazolyl; condensed heterocyclic groups containing at least one heteroatom chosen from sulphur, nitrogen and oxygen, for example benzothienyl such as 3-benzothienyl, benzofuryl, benzopyrrolyl, benzimidazolyl, benzoxazolyl, thionaphthyl, indolyl, indolinyl, quinolyl or isoquinolyl, purinyl, the term arylalkyl designates radicals in which the alkyl and aryl radical respectively can take the values defined above for these radicals; as examples of such arylalkyl radicals, there can be mentioned the following radicals: benzyl, diphenylmethyl, triphenylmethyl, naphthylmethyl, indenylmethyl, thienylmethyl such as 2-thienylmethyl, furylmethyl such as furfuryl, pyridylmethyl, pyridylthyl, pyrimidylmethyl or pyrrolylmethyl, it being understood that in the non-exhaustive list of examples of radicals as mentioned above, the alkyl radical can be represented by methyl just as well as by ethyl, propyl or butyl radicals such as, for example, in the phenylalkyl radicals such as phenylethyl, phenylpropyl or phenylbutyl;

the terms arylalkenyl and arylalkynyl designate radicals in which the alkenyl or alkynyl and aryl radicals respectively can take the values defined above for these radicals; as examples of such arylalkenyl radicals there can be mentioned for example the examples give above of arylalkyl radicals in which the alkyl radical is replaced by an alkenyl radical such as for example in the phenylvinyl or phenylallyl radicals, it being understood that in these radicals the phenyl radical can be replaced just as well by a naphthyl, pyridyl radical or also for example one of the aryl radicals as defined above; as examples of such arylalkynyl radicals, there can be mentioned for example the phenylethynyl radical.

As examples of alkyl radicals substituted by an aryl radical, there can be mentioned, for example, the arylalkyl radicals defined above.

As examples of alkenyl radicals substituted by an aryl radical, there can be mentioned, for example, the arylalkenyl radicals as defined above.

the term aryloxy radical preferably designates radicals in which the aryl radical is as defined above such as for example in phenoxy, the term arylalkoxy radical preferably designates radicals in which the aryl radical and the alkoxy radical represent the radicals as defined above such as for example in benzyloxy, phenylethoxy or phenylisopropoxy, the term arylthio radical preferably designates the radicals in which the aryl radical represents the radicals as defined above such as for example in phenylthio, pyridylthio or pyrimidylthio, imidazolylthio or N-methylimidazolylthio, the term alkylthio radical preferably designates the radicals in which the alkyl radical is as defined above such as for example in methylthio, ethylthio, propylthio, isopropylthio, butylthio, sec-butylthio, tert-butylthio, isopentylthio or isohexylthio, optionally substituted such as for example in hydroxymethylthio or aminoethylthio, the term haloalkylthio radical preferably designates the radicals in which the alkyl radical is as defined above and is substituted by one or more halogen atoms as defined above such as for example in bromoethylthio, trifluoromethylthio, trifluoroethylthio or also pentafluoroethylthio, the term arylalkylthio or alkylthio radical substituted by an aryl radical represents for example the benzylthio or phenethylthio radical.

In all the radicals which can be represented by or be carried by $R_1$, $R_2$, $R_3$ and $R_4$, as defined above, the sulphur atoms can be non-oxidized as in alkylthio, arylthio, cycloalkylthio radicals such as for example cyclohexylthio or on the other hand be oxidized to give alkylsulphinyl, cycloalkylsulphinyl, arylsulphinyl, alkylsulphonyl, cycloalkylsulphonyl or arylsulphonyl radicals:

the terms alkylsulphinyl and alkylsulphonyl radical designate alkylthio radicals in which the linear or branched alkyl radical can represent, for example, the values indicated above for the alkyl radical and in which the thio radical is oxidized into a sulphinyl or sulphonyl radical. There can be mentioned for example methylsulphinyl, ethylsulphinyl, methylsulphonyl or ethylsulphonyl radicals, the term arylsulphinyl and arylsulphonyl radical designates arylthio radicals, in which the aryl radical can represent, for example, the values indicated above for the aryl radical and in which the thio radical is oxidized into the sulphinyl or sulphonyl radical such as for example in the following radicals: phenyl-sulphinyl or -sulphonyl, pyridyl-sulphinyl or -sulphonyl, pyrimidyl-sulphinyl or -sulphonyl, imidazolyl-sulphinyl or -sulphonyl or N-methylimidazolyl-sulphinyl or -sulphonyl.

The carbamoyl and amino radicals which can be represented or carried by one or more of the optional substituents of the radicals defined in the products of formula (I) and in what follows, designate radicals in which the nitrogen atom has two radicals linked to it, which are identical or different, chosen from the hydrogen atom in order to give the amino radical; alkyl radicals as defined above to give monoalkyl- or dialkylamino radicals in which the linear or branched alkyl radicals contain 1 to 6 carbon atoms, all these radicals being optionally substituted as indicated above and hereafter.

The carbocyclic or heterocyclic radicals which can be represented by $R_6$, $R_7$, $R_8$ and $R_9$ can take the values defined above for these radicals and in particular the following values: phenyl, benzyl, phenethyl, naphthyl, indolyl, indolinyl, thienyl, furyl, pyrrolyl, pyridyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl.

When $R_6$ and $R_7$ on the one hand, $R_8$ and $R_9$ on the other hand or $R_{14}$ and $R_{15}$ again on the other hand, as defined above, form together with the nitrogen atom to which they are linked a heterocycle, it is, for example, one of the following rings: pyrrolyl, imidazolyl, indolyl, indolinyl, purinyl, pyrrolidinyl, piperidino, morpholino, piperazinyl, imidazolidinyl, pyrazolidinyl, thiomorpholinyl, azepine; these radicals can be optionally substituted by one or more radicals as defined previously and in particular by one or more radicals chosen from chlorine and fluorine atoms, the following radicals: methyl, ethyl, isopropyl, tert-butyl, methoxy, ethoxy, propoxy, benzoyl, methoxycarbonyl, ethoxycarbonyl, such as for example in methylpiperazinyl, fluoromethylpiperazinyl, ethylpiperazinyl, propylpiperazinyl, phenylpiperazinyl or benzylpiperazinyl: in these last two radicals, the phenyl and benzyl radicals can be substituted as indicated previously in the aryl, arylalkyl and arylalkenyl radicals, such as for example in chlorophenyl or trifluorophenyl.

The heterocycle which can be formed by $R_6$ and $R_7$ on the one hand, $R_8$ and $R_9$ on the other hand, respectively with the nitrogen atom to which they are linked, preferably represents a saturated heterocycle.

Similarly, in the products of formula (I), the carbamoyl or amino radicals are such that the radicals carried by the nitrogen atom are identical or different, can represent aliphatic or cyclized chains or can form with the nitrogen atom to which they are linked a heterocycle, as has been defined above for $R_6$, $R_7$, $R_8$, $R_9$.

The optionally substituted amino radical therefore designates the amino radical optionally substituted by one or two alkyl radicals chosen from alkyl radicals as defined above such as for example monoalkylamino in methylamino or ethylamino or isopropylamino or for example for dialkylamino in dimethylamino, diethylamino or also methylethylamino, these alkyl radicals being optionally substituted as indicated above, such as for example methoxymethyl, methoxyethyl, ethoxyethyl radicals.

By way of example and in a non-exhaustive manner, the term optionally substituted carbamoyl radical designates carbamoyl radicals optionally substituted on the nitrogen atom by one or two alkyl radicals optionally substituted as defined above, to form in particular an N-monoalkyl carbamoyl group such as N-methylcarbamoyl, N-ethylcarbamoyl or an N,N-dialkyl carbamoyl group, such as N,N-dimethylcarbamoyl, N,N-diethylcarbamoyl; an N-(hydroxyalkyl) carbamoyl group, such as N-(hydroxymethyl) carbamoyl, N-(hydroxyethyl) carbamoyl, phenylcarbamoyl; pyridylcarbamoyl; benzylcarbamoyl; N-methyl N-phenylcarbamoyl; pyridylmethylcarbamoyl. Furthermore, among the substituted alkyl radicals, there can also be mentioned alkyl radicals substituted by a carbamoyl radical as defined above, to form a carbamoylalkyl group such as carbamoylmethyl or carbamoylethyl.

The amino radical can be an alkoxycarbonylamino radical, this radical then preferably being the tert-butyloxycarbonyl-amino radical or the benzyloxycarbonylamino radical.

According to whether $m_1$ represents the value 0, 1, 2, 3 or 4, the —$(CH_2)_{m1}$— radical represents a single bond, the methylene radical, the ethylene, propylene, isopropylne or butylene radical.

The carboxy radical or radicals of the products of formula (I) can be salified or esterified by various groups known to a man skilled in the art amongst which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methyl-glucamine, among the esterification compounds, alkyl radicals to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, the following radicals: hydroxyl, alkoxy, acyl, acyloxy, alkylthio, amino or aryl such as, for example, in the chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, arylmonosulphonic such as benzenesulphonic and aryldisulphonic.

When $R_2$ and $R_3$ both represent a sulphur group, $R_2$ and $R_3$ being identical or different, in the preferred products of the invention, these sulphur groups do not necessarily have the same oxidation number.

Also a subject of the present invention is the products of formula (I) as defined above and corresponding to the formula ($I_A$):

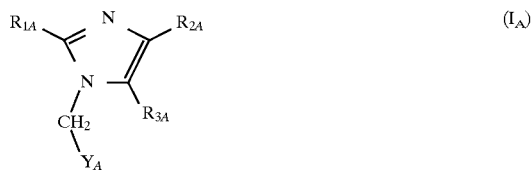

in which:

$R_{1A}$ represents a hydrogen atom, a hydroxyl, alkoxyl, formyl, dioxol, aryl, arylcarbonyl, arylthio radical, an alkylcarbonyl radical in which the alkyl radical is linear or branched, containing at most 6 carbon atoms, the aryl and alkyl radicals in all the radicals which can be represented by $R_1$ being optionally substituted by one or more identical or different radicals chosen from halogen atoms, hydroxyl, alkoxy and alkylthio radicals, containing at most 6 carbon atoms, acyl, free, salified, esterified or amidified carboxy, cyano, nitro radicals, amino radicals optionally substituted by one or two identical or different alkyl radicals containing at most 6 carbon atoms, cycloalkyl radicals containing 3 to 7 carbon atoms and phenyl radicals optionally substituted by one or more radicals chosen from halogen atoms, the following radicals: hydroxyl, alkyl and alkoxy containing at most 4 carbon atoms, trifluoromethyl, free, salified or esterified carboxy, cyano and tetrazolyl, $R_{2A}$ and $R_{3A}$, identical or different, are chosen from:

a) halogen atoms, the following radicals: mercapto, acyl, free, salified or esterified carboxy, nitro, cyano, b) the $R_{4A}$ and —$OR_{4A}$ radicals in which:
either $R_{4A}$ represents the $(CH_2)_{m3}$—$S(O)_{m2}$—$X_a$—$R_{10a}$ radical in which m3 represents the values 0 and 1, m2 represents the values 0 to 2 and either —X—$R_{10A}$ represents the amino radical or $X_a$ represents a single bond or the —NH, —NHCO—, —NH—CO—O—, —NH—CO—NH— and —N=CH—$NR_{11A}$ radicals with $R_{10a}$ representing an alkyl, alkenyl or aryl radical, these radicals being optionally substituted by one or more substituents chosen from halogen atoms, the following radicals: hydroxyl, alkyl and alkoxy containing at most 4 carbon atoms, trifluoromethyl, nitro, cyclohexyl, cyclopentyl, aryl optionally substituted by one or more identical or different radicals chosen from halogen atoms, the following radicals: hydroxyl, alkyl and alkoxy containing at most 6 carbon atoms, trifluoromethyl, free, salified or esterified carboxy, cyano, nitro, amino optionally substituted by one or two identical or different alkyl radicals containing at most 4 carbon atoms, and $R_{11A}$ represents the hydrogen atom or the values defined for $R_{10A}$, or $R_{4A}$ represents a hydrogen atom, an alkyl, alkenyl and acyl radical, these radicals being linear or branched and containing at most 6 carbon atoms, and being optionally interrupted by one or more heteroatoms chosen from sulphur, oxygen or nitrogen atoms, an amino radical optionally substituted by one or two identical or different alkyl radicals containing at most 6 carbon atoms, a cycloalkyl radical containing 3 to 6 carbon atoms or an aryl radical, the alkyl, alkenyl and aryl radicals of all the radicals which can be represented by $R_4$, being optionally substituted by one or more identical or different radicals chosen from:

halogen atoms, hydroxyl, mercapto, cyano, azido, nitro, $SO_3H$, free, salified, esterified or amidified carboxy radicals, alkyl, alkenyl, alkoxy, haloalkyl, alkylthio, acyl, acyloxy, acylthio, haloalkylthio, haloalkoxy radicals, these radicals containing at most 6 carbon atoms, aryl, arylalkyl, arylalkenyl, arylthio, aryloxy and arylalkoxy radicals in which the aryl radical is optionally substituted by one or more identical or different radicals chosen from halogen atoms, the following radicals: hydroxyl, alkyl and alkoxy containing at most 6 carbon atoms, trifluoromethyl, free, salified or esterified carboxy, cyano, nitro, amino optionally substituted by one or two identical or different alkyl radicals containing at most 4 carbon atoms, tetrazolyl and phenyl optionally substituted by one or more radicals chosen from halogen atoms, hydroxyl radicals, alkyl and alkoxy radicals containing at most 4 carbon atoms, trifluoromethyl and free, salified or esterified carboxy radicals, the

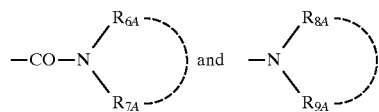

radicals in which:
either $R_{6A}$ and $R_{7A}$ or $R_{8A}$ and $R_{9A}$, being identical or different, are chosen from:
the hydrogen atom,
alkyl radicals containing at most 4 carbon atoms and optionally substituted by one or more identical or different radicals chosen from halogen atoms, the hydroxyl radical or alkoxy radicals containing at most 4 carbon atoms,
aryl and arylalkyl radicals in which the linear or branched alkyl radicals contain at most 4 carbon atoms, these aryl and arylalkyl radicals being optionally substituted by one or more radicals chosen from halogen atoms, hydroxyl, nitro, cyano, trifluoromethyl radicals, alkyl, alkoxy and acyl radicals containing at most 6 carbon atoms, amino radicals optionally substituted by one or two identical or different alkyl radicals containing at most 4 carbon atoms, free, salified or esterified carboxy radicals, tetrazolyl and phenyl radicals, optionally substituted by one or more radicals chosen from halogen atoms, hydroxyl, trifluoromethyl, nitro, cyano, free, salified or esterified carboxy and tetrazolyl radicals, or $R_{6A}$ and $R_{7A}$ or $R_{8A}$ and $R_{9A}$ form respectively with the nitrogen atom to which they are linked a monocyclic radical containing 5, 6 or 7 members or a radical constituted by condensed rings containing 8 to 14 members, these identical or different radicals optionally containing one or more other heteroatoms chosen from oxygen, nitrogen and sulphur atoms, and being optionally substituted by one or more radicals chosen from halogen atoms, hydroxyl, nitro, cyano, trifluoromethyl radicals, alkyl, alkoxy and acyl radicals containing at most 6 carbon atoms, amino radicals optionally substituted by one or two identical or different alkyl radicals containing at most 4 carbon atoms, free, salified, esterified or amidified carboxy, tetrazolyl, oxazolyl and phenyl radicals, optionally substituted by one or more radicals chosen from halogen atoms, hydroxyl, trifluoromethyl, nitro, cyano, free, salified or esterified carboxy and tetrazolyl radicals, or $R_{8A}$ and $R_{9A}$, identical or different, represent an acyl radical or one of $R_{8A}$ or $R_{9A}$ represents a carbamoyl, alkoxycarbonyl or benzyloxycarbonyl radical and the other is chosen from the values defined above for $R_{8A}$ and $R_{9A}$ or $R_{8A}$ and $R_{9A}$ form together with the nitrogen atom to which they are linked a phthalimido or succinimido radical, $Y_A$ represents the —$Y_{1A}$—B—$Y_{2A}$ radical in which:

$Y_{1A}$ represents an aryl radical optionally substituted by one or more radicals chosen from the dioxol radicals and the radicals which can be represented by $R_{2A}$ and $R_{3A}$, B represents a single bond between $Y_{1A}$ and $Y_{2A}$ or one of the following divalent radicals: —CO—, —O—, —NH—CO—, —CO—NH— or —O—$(CH_2)_p$— with p representing the values 1, 2 or 3, $Y_{2A}$ is defined as follows:
either, whatever the value of B is and $Y_{2A}$ being identical to or different from $Y_{1A}$, $Y_{2A}$ is chosen from the values defined for $Y_{1A}$,
or, if B represents a single bond, $Y_{2A}$ represents a hydrogen atom, a halogen atom, a cyano radical, a free, salified, esterified or amidified carboxy or carboxycarbonyl radical, a tetrazolyl radical or a $(CH_2)_{m3}$—$S(O)_{m2}$—$X_a$—$R_{10a}$ radical as defined above, the said products of formula ($I_A$) being in all possible racemic, enantiomeric and diastereoisomeric isomer forms, as well as the addition salts with mineral and organic acids or with mineral and organic bases of said products of formula ($I_A$).

A particular subject of the invention is the products of formula (I) as defined above and corresponding to formula ($I_B$):

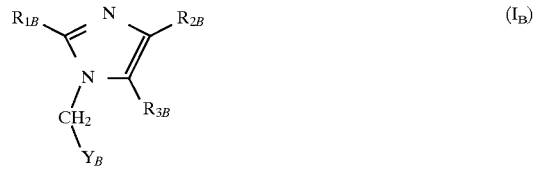

in which:
$R_{1B}$ represents the hydrogen atom and the alkoxy, dioxol, phenyl, benzoyl and phenylthio radicals in which the phenyl radical is optionally substituted by one or more radicals chosen from halogen atoms, the following radicals: hydroxyl, alkyl and alkoxy containing at most 4 carbon atoms, trifluoromethyl, cyano, free, salified or esterified carboxy and tetrazolyl, $R_{2B}$ and $R_{3B}$, identical or different, are chosen from:

a) halogen atoms; the mercapto radical; free, salified or esterified carboxy radicals; the hydroxyl radical; alkoxy and acyl radicals, containing at most 6 carbon atoms; cyano radicals; nitro radicals; benzoyl radicals;

b) the $R_{4B}$ and —$OR_{4B}$ radicals, in which:

either $R_{4B}$ represents the $(CH_2)_{m3}$—$S(O)_{m2}$—$X_B$—$R_{10B}$ radical in which $m_3$ represents the values 0 and 1, $m_2$ represents the values 0 to 2 and either —$X_B$—$R_{10B}$ represents the amino radical or $X_B$ represents a single bond or the —NH, —NHCO—, —NH—CO—O—, —NH—CO—NH— and —N=CH—$NR_{11B}$ radicals with $R_{10B}$ representing a methyl, ethyl, propyl, vinyl, allyl, pyridyl, phenyl, pyrimidinyl, tetrazolyl, thiazolyl, diazolyl, quinolyl or furyl radical, all these alkyl and alkenyl radicals being optionally substituted by one or more substituents chosen from halogen atoms, hydroxyl and alkoxy radicals containing at most 4 carbon atoms, trifluoromethyl, nitro, cyclohexyl, cyclopentyl, pyridyl, pyrimidinyl, thienyl, tetrazolyl and phenyl radicals, all the phenyl radicals being optionally substituted by one or more radicals chosen from halogen atoms, hydroxyl radicals, alkoxy radicals containing at most 4 carbon atoms, cyano and tetrazolyl radicals, and $R_{11B}$ represents the hydrogen atom or the values defined for $R_{10B}$, or $R_{4B}$ represents a hydrogen atom or a linear or branched alkyl or alkenyl radical containing at most 6 carbon atoms, the following radicals: cyclohexyl, phenyl, pyridyl, pyrimidinyl, tetrazolyl or imidazolyl, all these radicals being optionally substituted by one or more identical or different radicals chosen from:

halogen atoms, hydroxyl, mercapto, acylthio, trifluoromethyl, trifluoromethylthio, trifluoromethoxy, cyano, azido, nitro, formyl, —$SO_3H$, free, salified, esterified or amidified carboxy radicals, alkyl, alkylthio, acyl, acyloxy and alkoxy radicals containing at most 6 carbon atoms, the phenyl and phenylthio radicals, all these radicals being themselves optionally substituted by one or more radicals chosen from halogen atoms, the hydroxyl radical, alkoxy radicals containing at most 4 carbon atoms, free, salified, esterified or amidified carboxy, nitro and phenyl radicals, isoxazolyl, pyrrolidinyl, pyrrolidinylcarbonyl, pyridyl, pyrimidyl, thiazolyl, diazolyl, piperidinyl, tetrazolyl, tetrahydrofurannyl radicals, all these radicals being optionally substituted by a methyl, ethyl or nitro radical, the

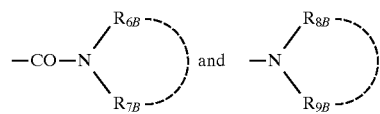

radicals in which:

either $R_{6B}$, $R_{7B}$, $R_{8B}$ and $R_{9B}$, identical or different, are chosen from the hydrogen atom, alkyl radicals containing at most 4 carbon atoms and optionally substituted by one or more identical or different radicals chosen from halogen atoms, the hydroxyl radical or alkoxy radicals containing at most 4 carbon atoms, and phenyl, benzyl, phenethyl, azepine, piperidyl, morpholine, pyrrolidinyl, piperazinyl radicals, or on the one hand $R_{6B}$ and $R_{7B}$ and on the other hand $R_{8B}$ and $R_{9B}$ form respectively with the nitrogen atom to which they are linked a heterocyclic radical, these identical or different radicals being chosen from the following radicals: imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepine, indolyl, these radicals being optionally substituted by one or more identical or different radicals chosen from halogen atoms, hydroxyl, nitro, cyano, acyl, trifluoromethyl radicals, alkyl and alkoxy radicals, these radicals containing at most 4 carbon atoms, free, salified, esterified or amidified carboxy, tetrazolyl, oxazolyl and phenyl radicals, $Y_B$ represents the phenyl radical optionally substituted by one or more radicals chosen from halogen atoms, dioxol radicals, cyano, free, salified or esterified carboxy or carboxycarbonyl radicals, the tetrazolyl radical and the —$(CH_2)_{m3}$—$S(O)_{m2}$—$X_B$—$R_{10B}$ radical as defined above, said products of formula ($I_B$) being in all possible racemic, enantiomeric and diastereoisomeric isomer forms, as well as the addition salts with mineral and organic acids or with mineral and organic bases of said products of formula ($I_B$).

A quite particular subject of the invention is the products of formula (I) as defined above and corresponding to formula ($I_B$), as defined above, in which one or both of the following conditions are fulfilled:

Y represents the phenyl radical optionally substituted by two radicals forming together a dioxol radical, and optionally by one or more radicals chosen among the halogen atoms, and the alkoxy and the free, salified or esterified carboxy and carboxycarbonyl radicals, or at least one of $R_{2B}$ and $R_{3B}$ is chosen from the following radicals:

$(CH_2)_{m3}$—$S(O)_{m2}$—$X_B$—$R_{10B}$ as defined above, alkyl substituted by a free, salified, esterified or amidified carboxy radical;

formyl;

free, salified, esterified or amidified carboxy;

and aryl; said products of formula ($I_B$) being in all possible racemic, enantiomeric and diastereoisomeric isomer forms, as well as the addition salts with mineral and organic acids or with mineral and organic bases of said products of formula ($I_B$).

The $(CH_2)_{m3}$—$S(O)_{m2}$—$X_B$—$R_{10B}$ radical can represent in particular the radicals in which $X_b$—$R_{10b}$ represents the following radicals:

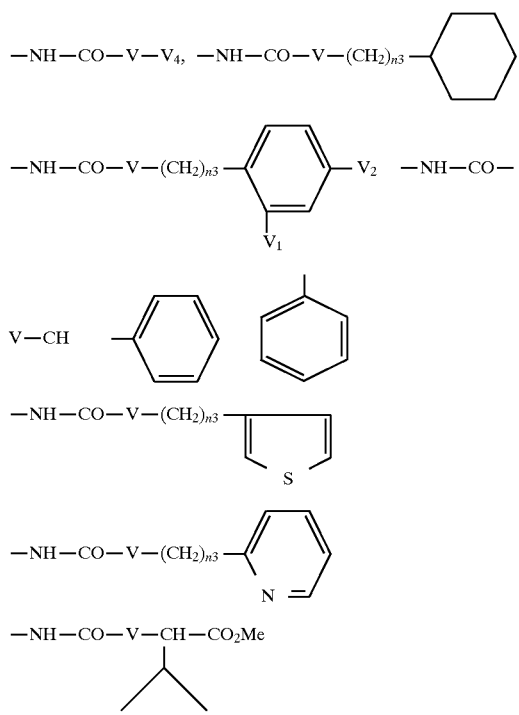

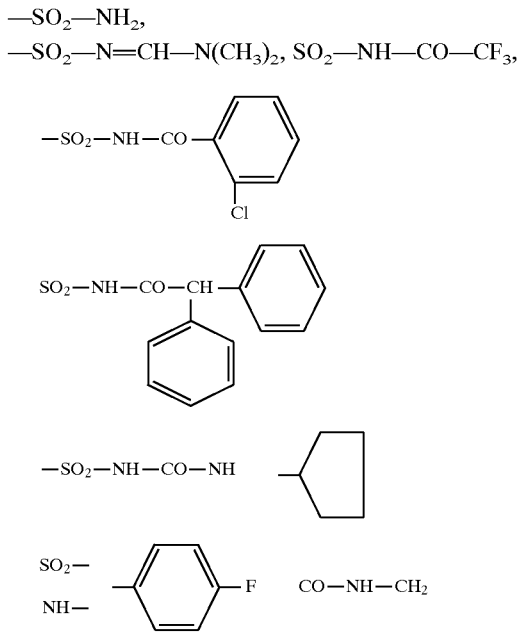

with n3 representing an integer from 0 to 3, V represents a single bond or the —NH— and —O— radicals, $V_1$ and $V_2$ identical or different represent a hydrogen atom, a halogen atom in particular chlorine or fluorine and an alkoxy radical in particular methoxy and $V_4$ represents a hydrogen atom or an alkyl or alkenyl radical such as in particular methyl, ethyl, propyl, butyl, vinyl or allyl.

The $(CH_2)_{m3}$—$S(O)_{m2}$—$X_B$—$R_{10B}$ radical as defined above can therefore represent for example and in a non-exhaustive manner the following radicals:

—$SO_2$—$NH_2$,
—$SO_2$—$N$=$CH$—$N(CH_3)_2$, $SO_2$—$NH$—$CO$—$CF_3$,

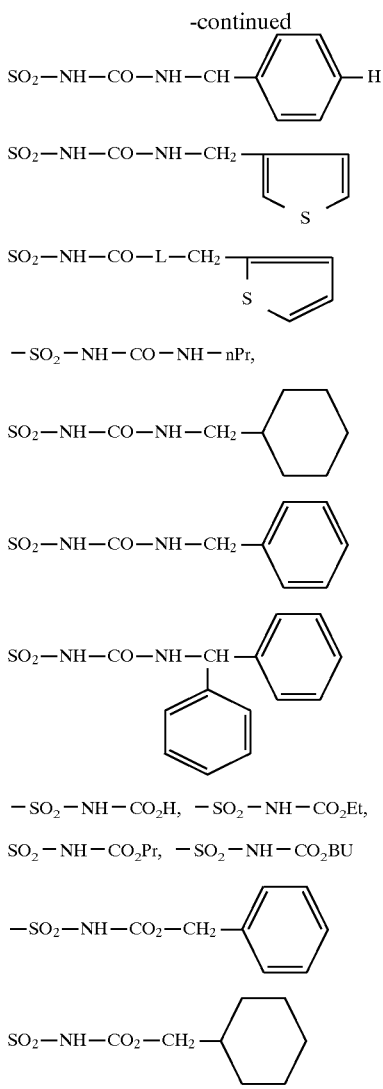

A more particular subject of the invention is the products of formula (I) as defined above and corresponding to formula ($I_C$), in which:

$R_1$ represents the hydrogen atom, an alkoxy, dioxol, phenyl, benzoyl and phenylthio radical in which the phenyl radical is optionally substituted by a hydroxyl or alkoxy radical containing at most 4 carbon atoms, $R_2$ and $R_3$, identical or different, are chosen from halogen atoms; the carboxy radical, free, salified or esterified by an alkyl radical containing at most 4 carbon atoms; the formyl radical; and the following radicals: tetrazolyl, phenyl, phenylthio, phenylsulphonyl, phenylsulphinyl, alkyl containing at most 4 carbon atoms, alkylthio, alkylsulphonyl and alkylsulphinyl, all these radicals being optionally substituted by one or more radicals chosen from halogen atoms, hydroxyl radicals, alkoxy radicals containing at most 4 carbon atoms, free, salified or esterified carboxy radicals and the phenyl radical itself optionally substituted by a hydroxyl or alkoxy radical containing at most 4 carbon atoms, and Y represents the phenyl radical optionally substituted by two radicals forming together the dioxol radicals and by one or more halogen atoms, said products of formula (I) being in all possible racemic, enantiomeric and diastereoisomeric isomer forms, as well as the addition salts with mineral and organic acids or with mineral and organic bases of said products of formula (I).

A quite particular subject of the invention is the products of formula (I) as defined above and corresponding to formula (I$_D$), in which:

R$_1$ represents the hydrogen atom, the 1,3-dioxolan, phenyl, benzoyl and phenylthio radical in which the phenyl radical is optionally substituted by a hydroxyl or alkoxy radical containing at most 4 carbon atoms, R$_2$ represents a halogen atom, an alkylthio radical in which the linear or branched alkyl radical, containing at most 4 carbon atoms, is optionally substituted by a phenyl radical itself optionally substituted by an alkoxy radical and the phenylthio radical in which the phenyl radical is optionally substituted by an alkoxy radical, R$_3$ represents a formyl or free, esterified, salified or amidified carboxy radical, and Y represents a phenyl radical substituted by a halogen atom and by two radicals forming together a dioxol radical, said products of formula (I) being in all possible racemic, enantiomeric and diastereoisomeric isomer forms, as well as the addition salts with mineral and organic acids or with mineral and organic bases of said products of formula (I).

Among the products which are a subject of the invention, there can be mentioned quite particularly the products of formula (I) corresponding to the following formulae:

1-((6-chloro-1,3-benzodioxol-5-yl) methyl)-4-(((4-methoxyphenyl) methyl) thio)-2-(phenylthio)-1H-imidazole-5-carboxaldehyde 4-bromo-1-((6-chloro-1,3-benzodioxol-5-yl) methyl)-2-phenyl-1H-imidazole-5-carboxylic acid 1-((6-chloro-1,3-benzodioxol-5-yl) methyl)-4-(((4-methoxyphenyl) methyl) thio)-2-(phenylthio)-1H-imidazole-5-carboxylic acid 1-((6-chloro-1,3-benzodioxol-5-yl) methyl)-4-(4-methoxyphenyl) thio)-2-(phenylthio)-1H-imidazole-5-carboxylic acid 1-((6-chloro-1,3-benzodioxol-5-yl) methyl)-2,4-bis(4-(methoxyphenyl) thio)-1H-imidazole-5-carboxylic acid, 1-((6-chloro 1,3-benzodioxol-5-yl) methyl) 4-((3,4-dimethoxyphenyl) thio) 2-(1,3-dioxolan-2-yl) 1H-imidazol 5-carboxylic acid.

Also a subject of the invention is a preparation process for the products of formula (I), as defined above, characterized in that:
either a compound of formula (II):

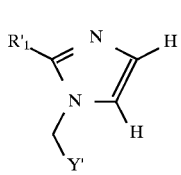

in which R'$_1$ has the meaning indicated above for R$_1$, in which the optional reactive functions are optionally protected by protective groups, is subjected to a reaction with a compound of formula (III):

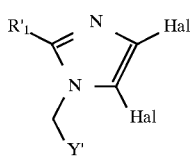

in which Hal represents a halogen atom, and Y' has the meaning indicated above for Y, in which the optional reactive functions are optionally protected by protective groups, in order to obtain the product of formula (IV$_1$):

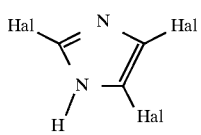

in which R'$_1$ and Y' have the meanings indicated above, which product of formula (IV$_1$) can be subjected to a halogenation reaction, in order to obtain the product of formula (IV$_2$):

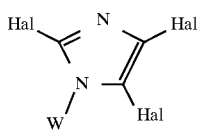

in which R'$_1$, Hal and Y have the meanings indicated above, or a compound of formula (VIII):

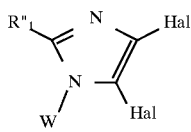

in which Hal has the meaning indicated above, is subjected either to a reaction with the compound of formula (III) as defined above, or to the action of a protective group P, in order to obtain a product of formula (IX):

in which Hal has the meaning indicated above and W represents either —CH$_2$—Y' with Y as defined above, or P which represents a protective group of the nitrogen atom, which product of formula (IX) is subjected to a halogen-metal exchange reaction then to a reaction with an electrophilic compound of formula (X), (X'), (XI), (XII) or (XII'):

| L$_1$—CHO | (X) |
| L$_1$—CO—Cl | (X') |
| (—S—L$_1$)$_2$ | (XI) |
| L$_1$SO$_2$—S—L'$_1$ | (XII) |
| L$_1$SO$_2$—Cl | (XII') | in which L$_1$ and L'$_1$, identical or different, represent an alkyl, alkenyl or aryl radical, as defined above, in order to obtain a product of formula (XIII):

in which Hal and W have the meanings indicated above, R"$_1$ represents an aryl- or alkyl-carbonyl, aryl- or alkyl-hydroxymethyl or arylthio radical in which the aryl and alkyl radicals have the meanings indicated above and in which the optional reactive functions are optionally protected by protective groups, which products of formulae (IV$_2$) and (XIII) can be subjected to a halogen-metal exchange reaction on one of the halogen atoms then to a reaction with CO$_2$ or DMF or an electrophilic compound of formula (V$_a$), (V$_b$), (VI$_a$), (VI$_b$) or (VI$_c$):

$$(-S-Z_1)_2 \quad \text{or} \quad (Va)$$

$$MeSO_2SZ_1 \quad \text{or} \quad (Vb)$$

$$Cl-\underset{\underset{O}{\|}}{C}-Oalk \quad \text{or} \quad (VI_a)$$

$$(alk\text{-}O)_2-\underset{\underset{O}{\|}}{C} \quad \text{or} \quad (VI_b)$$

$$(alk\text{-}O-\underset{\underset{O}{\|}}{C})_2 \quad (VI_c)$$

in which Z$_1$ represents an alkyl, alkenyl or aryl radical, optionally substituted, in which the optional reactive functions are optionally protected by protective groups, and alk represents an alkyl radical containing at most 4 carbon atoms, in order to obtain the compound of formula (I$_1$):

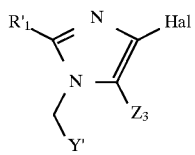
(I$_1$)

or the compound of formula (XIV):

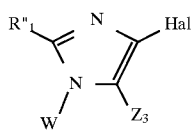
(XIV)

respectively in which R'$_1$, R"$_1$, Hal, Y' and W have the meanings indicated above and Z$_3$ represents the carboxy, formyl radical, S—Z$_1$ as defined above, or the K—O-alk radical in which K represents the $$-\underset{\underset{O}{\|}}{C}- \quad \text{or} \quad -\underset{\underset{O}{\|}}{C}-\underset{\underset{O}{\|}}{C}-$$

radical and alk has the meaning indicated above, which compounds of formula (I$_1$) or (XIV) when Z$_3$ represents a formyl radical or esterified carboxy radical, can be subjected to a reaction with a compound of formula (VII):

$$Z_2-S-M \quad (VII)$$

in which S represents a sulphur atom, M represents a metal such as sodium, potassium or copper and Z$_2$ represents an alkyl, alkenyl or aryl radical, optionally substituted, in which the optional reactive functions are optionally protected by protective groups in order to obtain the compound of formula (I$_2$):

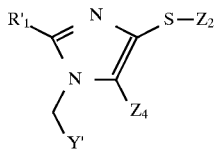
(I$_2$)

or the compound of formula (XV):

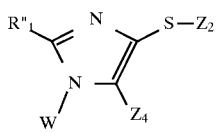
(XV)

respectively in which R'$_1$, R"$_1$, Y', Z$_2$ and W have the meanings indicated above, and Z$_4$ represents the formyl radical or esterified carboxy radical, which products of formulae (I$_2$) and (XV), when Z$_4$ represents the formyl radical, can be subjected to an oxidation or reduction reaction in order to obtain a product of formula (I$_3$):

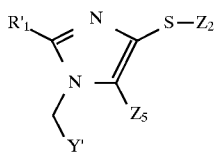
(I$_3$)

or a product of formula (I$_4$):

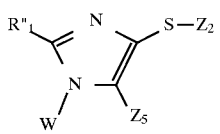
(I$_4$)

respectively in which R'$_1$, R"$_1$, Z$_2$, Y' and W have the meanings indicated above, and Z$_5$ represents the CH$_2$OH radical or the carboxy radical, free or esterified by a linear or branched alkyl radical containing at most 6 carbon atoms, which products of formula (XV) or (I$_4$), in the case where W represents P as defined above and after release of the amine function blocked by P as defined above, are reacted with the compound of formula (III) as defined above, in order to obtain a product of formula (I$_5$):

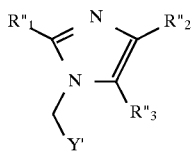
(I$_5$)

in which R"$_1$ and Y' have the meanings indicated above, and one of R"$_2$ and R"$_3$ indifferently represents Z$_4$ or Z$_5$ as defined above and the other represents S—Z$_2$, as defined above, or a compound of formula (XVI):

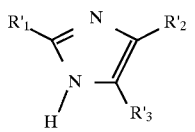
(XVI)

in which R'$_1$ has the meaning indicated above and R'$_2$ and R'$_3$ have the meanings indicated above for R$_2$ and R$_3$ respectively in which the optional reactive functions are optionally protected by protective groups, is subjected to a reaction with the compound of formula (III) as defined above, in order to obtain a product of formula (I'):

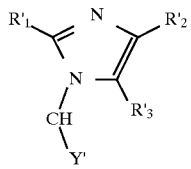

in which R'$_1$, R'$_2$, R'$_3$ and Y' have the definitions indicated above, which products of formulae (I$_1$), (I$_2$), (I$_3$), (I$_4$), (XIV), (XV), (I$_5$) and (I') can be products of formula (I) and which, in order to obtain products or other products of formula (I), can be subjected, if desired and if necessary, to one or more of the following conversion reactions, in any order:

a) an esterification reaction of the acid function, b) a saponification reaction of the ester function into an acid function, c) a conversion reaction of the ester function into an acyl function, d) a conversion reaction of the cyano function into an acid function, e) a conversion reaction of the acid function into an amide function, then optionally into a thioamide function, f) a reduction reaction of the carboxy function into an alcohol function, g) a conversion reaction of the alkoxy function into a hydroxyl function, or also of the hydroxyl function into an alkoxy function, h) an oxidation reaction of the alcohol function into an aldehyde, acid or ketone function, i) a conversion reaction of the formyl radical into a carbamoyl radical, j) a conversion reaction of the carbamoyl radical into a nitrile radical, k) a conversion reaction of the nitrile radical into a tetrazolyl, l) an oxidation reaction of the alkylthio or arylthio group into a corresponding sulphoxide or sulphone, m) a conversion reaction of the sulphide, sulphoxide or sulphone function into a corresponding sulphoximine function, n) a conversion reaction of the oxo function into a thioxo function, o) a conversion reaction of the

radical into a

radical then if necessary again into an

radical with L$_1$ as defined above, p) a conversion reaction of the acid function into a

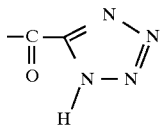

function, q) a conversion reaction of the beat-keto-sulphoxide function into an alpha-keto thio ester function, r) a conversion reaction of a carbamate into urea and in particular of a sulphonylcarbamate into sulphonylurea, s) an elimination reaction of the protective groups which can be carried by the protected reactive functions, t) a salification reaction by a mineral or organic acid or by a base in order to obtain the corresponding salt, u) a resolution reaction of racemic forms into resolved products, said products of formula (I) thus obtained being in all possible racemic, enantiomeric and diastereoisomeric isomer forms.

Under preferred conditions for implementing the invention, the process described above can be carried out in the following manner. In the product of formula (III), the halogen atom preferably represents a bromine atom but can also represent a chlorine or iodine atom. The condensation reaction of the imidazoles of the formulae as defined above (II), (VIII), (XVI), (XV) and (I$_4$) (in the case of the products of formulae (XV) and (I$_4$), when W represents P and after deprotection of the nitrogen atom), with the compound of formula (III) as defined above, in order to obtain the products of formulae (IV$_1$), (IX) respectively when W represents Y', (I$_5$) and (I') respectively as defined above can be carried out in a solvent such as for example dimethylformamide or also dimethylacetamide, tetrahydrofuran, dimethoxyethane or dimethylsulphoxide under reflux of the solvent or at ambient temperature, preferably under agitation; the reaction is preferably carried out in the presence of a base such as for example sodium or potassium hydride or also of sodium or potassium carbonate, sodium or potassium methylate or ethylate or tert-butylate.

The halogenation reaction of the compound of formula (IV$_1$) as defined above into a compound of formula (IV$_2$) as defined above, can be carried out under the usual conditions known to a man skilled in the art and in particular by bromination using NBS in CH$_2$Cl$_2$ or also Br$_2$ in acetic acid.

The compounds of formulae (IV$_2$), (IX) and (XIII) as defined above can be subjected to a halogen metal exchange reaction on the halogen atom by reaction with an organo metallic compound such as nBuli or EtMgBr in a solvent such as THF at a temperature of approximately −78° C. for Buli and ambient temperature for EtMgBr.

The carboxylation reactions by CO$_2$ and the formylation reactions by DMF of the compounds of formulae (IV$_2$) and (XIII) into compounds of formulae (I$_1$) and (XIV) respectively can be carried out according to the usual conditions known to a man skilled in the art, that is for example in THF at ambient temperature.

Z$_1$ and Z$_2$, identical or different, represent an alkyl, alkenyl or aryl radical such that Z$_1$—S— and Z$_2$—S— represent the corresponding values defined above for R$_2$ and R$_3$ in which the optional reactive functions are optionally protected by protective groups.

L$_1$ and L$_1'$, identical or different, represent an alkyl, alkenyl or aryl radical such that R$_{1''}$ represents the corresponding values chosen from the values of $R_1$ as defined above in which the optional reactive functions are optionally protected by protective groups.

The reaction of the compound of formula $(IV_2)$ or (XIII) as defined above with the compound of formula $(VI_a)$, $(VI_b)$ or $(VI_c)$, as defined above, in order to obtain the corresponding compound of formula $(I_1)$ or (XIV) respectively as defined above can be carried out in an identical manner by using EtMgBr as the metallation agent in THF at ambient temperature.

The reaction of the compounds of formulae $(IV_2)$ and (XIII) with the compounds of formula $(V_a)$ or $(V_b)$ can be carried out according to the usual conditions known to a man skilled in the art, that is, for example, in THF at ambient temperature.

The reaction of the compound of formula (IX) with the compounds of formulae (X), (X'), (XI), (XII) and (XII') can be carried out according to the usual conditions known to a man skilled in the art, that is, for example, in THF at ambient temperature.

The amine function of the compounds of formulae (XV) and $(I_4)$ as defined above, protected by P as defined above, can be released under the usual conditions known to a man skilled in the art and in particular when P represents the $-CH_2-O-(CH_2)_2-Si(CH_3)_3$ radical, the hydrogen atom can be released in TFA or also in the presence a fluoride ion.

The saponification reaction can be carried out according to the usual methods known to a man skilled in the art, such as for example in a solvent such as methanol or ethanol, dioxane or dimethoxyethane, in the presence of soda or potash or also caesium carbonate.

The reduction or oxidation reactions of the products of formulae $(I_2)$ and (XV) into the products of formulae $(I_3)$ and $(I_4)$ respectively can be carried out according to the usual methods known to a man skilled in the art.

According to the values of $R'_1, R''_1, R'_2, R''_2, R'_3, R''_3$, the products of formulae $(I_1)$, $(I_2)$, $(I_3)$, $(I_4)$, $(I_5)$, (XIV), (XV) and (I') constitute or do not constitute products of formula (I) and can produce products of formula (I), or be converted into other products of formula (I) by being subjected to one or more of reactions a) to u) indicated above.

In this way the various reactive functions which can be carried by certain compounds of the reactions defined above can, if necessary, be protected: thay are for example the hydroxyl, acyl, free carboxy radicals or also the amino and monoalkylamino radicals which can be protected by appropriate protective groups.

The following non-exhaustive list of examples of the protection of reactive functions can be mentioned:

hydroxyl groups can be protected for example by alkyl radicals such as tert-butyl, trimethylsilyl, tert-butyldimethylsilyl, methoxymethyl, tetrahydropyrannyl, benzyl or acetyl, amino groups can be protected for example by acetyl, trityl, benzyl, tert-butoxycarbonyl, phthalimido radicals or others radicals known from the chemistry of peptides, acyl groups such as the formyl group can be protected for example in the form of cyclic or non-cyclic ketals or thioketals such as dimethyl or diethylketal or ethylene dioxyketal, or diethylthioketal or ethylenedithioketal, the acid functions of the products described above can be, if desired, amidified by a primary or secondary amine for example in methylene chloride in the presence, for example, of 1-ethyl-3-(dimethylaminopropyl) carbodiimide hydrochloride at ambient temperature, the acid functions can be protected for example in the form of esters formed with easily cleavable esters such as benzylic or ter butylic esters or esters known from the chemistry of peptides.

The reactions to which the products of formulae $(I_1)$, $(I_2)$, $(I_3)$, $(I_4)$, $(I_5)$, (XIV), (XV) and (I'), as defined above, can be subjected, if desired or if necessary, can be carried out, for example, as indicated hereafter.

a) The products described above can, if desired, be the subject, on the optional carboxy functions, of esterification reactions which can be carried out according to the usual methods known to a man skilled in the art.

b) The optional conversions of the ester functions into an acid function of the products described above can be, if desired, carried out under the usual conditions known to a man skilled in the art in particular by acid or alkaline hydrolysis for example by soda or potash in an alcoholic medium such as, for example, in methanol or also by hydrochloric or sulphuric acid.

c) The addition reaction on the ester function

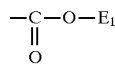

in which $E_1$ can represent an alkyl or aryl radical optionally substituted and optionally protected as an acyl function

can be carried out in particular by the action of the carbonaceous anion

in which $E_2$, $E_3$ and $E_4$, identical or different are chosen from the hydrogen atom, the following radicals: alkyl, alkylthioaryl, alkylsulphoxide, arylsulphoxide, alkylsulphone, arylsulphone, acyl, free, salified, esterified or amidified carboxy, the alkyl, alkylthio and aryl radicals being optionally substituted and optionally protected as indicated above.

Such a reaction is carried out in particular as described in the experimental part, or according to the usual methods known to a man skilled in the art.

d) The optional cyano functions of the products described above can be, if desired, converted into an acid function under the usual conditions known to a man skilled in the art for example by a double hydrolysis carried out in an acid medium such as for example in a mixture of sulphuric acid, glacial acetic acid and water, these three compounds being preferably in equal proportions, orso in a mixture of soda, ethanol and water under reflux.

e) The conversion reaction of the acid function into an amide function can in particular be carried out by first forming an acid chloride according to the usual conditions known to a man skilled in the art and for example by the action of $SOCl_2$ then by amidifying as described above, or also by direct amidification of the above acid.

In particular the radical

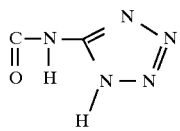

can be obtained by converting the acid function into an acid chloride, in particular by the action of $SOCl_2$ in a solvent such as for example toluene, or benzene, then by reacting the amine

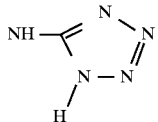

The amide thus obtained can then, if desired, be converted into a thioamide by the action in particular of a LAWESSON reagent in toluene.

f) The optional free or esterified carboxy functions of the products described above can be, if desired, reduced to an alcohol function by methods known to a man skilled in the art: the optional esterified carboxy functions can be, if desired, reduced to an alcohol function by methods known to a man skilled in the art and in particular by lithium aluminium hydride in a solvent such as for example tetrahydrofuran or also dioxane or ethyl ether.

The optional free carboxy functions of the products described above can be, if desired, reduced to an alcohol function in particular by boron hydride.

g) The optional alkoxy functions such as in particular methoxy of the products described above can be, if desired, converted into a hydroxyl function under the usual conditions known to a man skilled in the art for example by boron tribromide in a solvent such as for example methylene chloride, by pyridine hydrobromide or hydrochloride or also by hydrobromic or hydrochloric acid in water or trifluoroacetic acid under reflux.

h) The optional alcohol functions of the products described above can be, if desired, converted into an aldehyde or acid function by oxidation under the usual conditions known to a man skilled in the art such as for example by the action of manganese oxide in order to obtain the aldehydes or Jones reagent in order to obtain the acids.

i) j) The conversion reactions of the formyl radical into a carbamoyl radical and the carbamoyl radical into a nitrile radical, are achieved in particular for $R_3$ and $R_4$ according to the usual conditions known to a man skilled in the art, such as for example passage via the keto nitrile and displacement by an amine (Chem. Comm. 1971, p. 733).

k) The optional nitrile functions of the products described above can be, if desired, converted into tetrazolyl under the usual conditions known to a man skilled in the art such as for example by the cycloaddition of a metal azide such as for example sodium azide or a trialkyltin azide on the nitrile function as indicated in the method described in the article referenced as follows:

J. Organometallic Chemistry., 33, 337 (1971) KOZIMA S. et al.

l) The optional alkylthio or arylthio groups of the products described above can be, if desired, converted into thecorresponding sulphoxide or sulphone functions under the usual conditions known to a man skilled in the art such as for example by peracids such as for example peracetic acid or metachloroperbenzoic acid or also by ozone, oxone, sodium periodate in a solvent such as for example methylene chloride or dioxane at ambient temperature.

The obtaining of the sulphoxide function can be encouraged by an equimolar mixture of the product containing an alkylthio or arylthio group and the reagent such as in particular a peracid.

The obtaining of the sulphone function can be encouraged by a mixture of the product containing an alkylthio or arylthio group with an excess of reagent such as in particular a peracid.

m) The optional sulphide, sulphoxide or sulphone functions of the products described above can be, if desired, converted into the corresponding sulphoximine functions under the usual conditions known to a man skilled in the art: non-exhaustive examples of the preparation of products containing a sulphoximine function are described below.

Thus for example for the preparation of compounds such as the N-(arylsulphonyl) sulphoximines and for example in the case where the aryl group which is represented by X' is a toluene radical, the sulphoximine can be obtained by the action of paratoluenesulphonyl nitride on the corresponding sulphoxide namely $—S(O)CH_3$ preferably in the presence of copper as indicated, for example, in the following reference:

J. A. C. S., 95, pp. 4287 (1973) JOHNSON C. R. et al.

Another method also used consists of treating N-tosylsulphilimine, itself prepared from the sulphide by the action, for example, of chloramine "T", with an oxidizing agent such as for example, sodium hypochlorite under phase transfer conditions as indicated, for example, in the following reference:

J. Org. Chem., 49, pp. 2282 (1984) AKUTAGAWA K. et al.

n) The conversion reaction of the oxo function into a thioxo function can be carried out in particular by a LAWESSON reagent under the conditions defined above.

o) The conversion reaction of the

radical into an

radical can in particular be carried out using manganese oxide in dioxane.

The reverse conversion reaction of the

into an

radical can in particular be carried out using sodium borohydride in ethanol.

p) The conversion reaction of the acid function into a tetrazolylcarboxy function can be carried out for example by preliminary conversion of the acid function into an acid chloride as indicated above, then by the action of Cu—C≡N, according to the usual conditions known to a man skilled in the art on the acid chloride thus obtained, in this way the

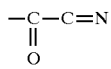

radical is obtained which can be converted into a

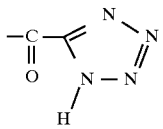

radical for example by the action of the Sn(Bu)₃N₃ compound in toluene, q) the conversion reaction of the beta keto sunphoxide function into an alpha keto thioester function, can be carried out by bromination in the alpha position of the ketosulphoxide for example by the action of NBS in for example methylene chloride then by a PUMMERER reaction carried out in a mixture of trifluoroacetic acid and methylene chloride or also a mixture of sulphuric acid and dioxane.

In particular, as is defined above in c) and q), the following reaction diagram can be implemented:

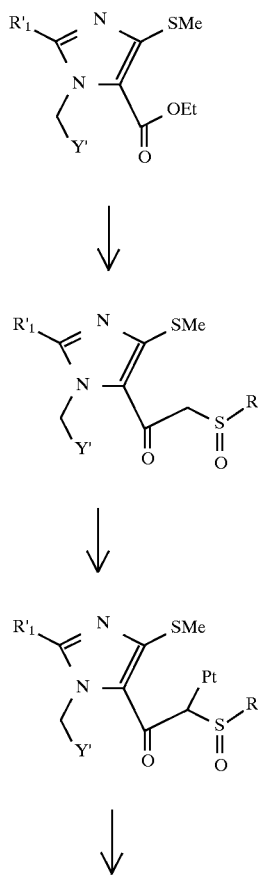

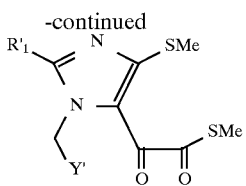

in which compounds R'₁ and Y' have the meanings indicated above, and R represents an optionally substituted alkyl or aryl radical as indicated above.

r) The conversion reaction of a carbamate into urea and in particular of a sulphonylcarbamate into sulphonylurea, can be carried out for example under reflux of a solvent such as for example toluene in the presence of the pertinent amine.

s) The elimination of protective groups such as for example those indicated above can be carried out under the usual conditions known to a man skilled in the art in particular by acid hydrolysis carried out with an acid such as hydrochloric, benzene sulphonic or paratoluene sulphonic, formic or trifluoroacetic acid or also by catalytic hydrogenation.

The phthalimido group can be eliminated by hydrazine.

A list of different protective groups which can be used will be found for example in the Patent BF 2,499,995.

t) The products described above can, if desired, be the subject of salification reactions for example using a mineral or organic acid or using a mineral or organic base according to the usual methods known to a man skilled in the art.

u) The possible optically-active forms of the products described above can be prepared by resolution of the racemics according to the usual methods known to a man skilled in the art.

Illustrations of such reactions defined above are given in the preparation of the examples described hereafter.

The compounds of formula (I) as defined above as well as their addition salts with acids have useful pharmacological properties.

The products of formula (I) as defined above are endowed with antagonistic properties for the endothelin receptors and are therefore in particular inhibitors of the effects of endothelin, in particular of the vaso-constrictive and hypertensive effects induced by endothelin. In particular an anti-ischemic effect is noted, the vaso-constrictive activity of endothelin being eliminated.

The products of formula (I) are also capable of opposing the stimulating effects of endothelin at the level of all cell types, in particular smooth muscle cells, neuronal cells and bone cells.

These properties justify their use in therapeutics and also a subject of the invention is as medicaments, the products as defined by formula (I) above, the said products of formula (I) being in all possible racemic or optically-active isomer forms, as well as the addition salts with pharmaceutically acceptable mineral and organic acids or mineral and organic bases of said products of formula (I).

A particular subject of the invention is, as medicaments, the products of formulae (I$_A$) and (I$_B$) as defined above, said products of formulae (I$_A$) and (I$_B$) being in all possible racemic or optically-active isomer forms, as well as the addition salts with pharmaceutically acceptable mineral or organic acids or mineral and organic bases of said products of formulae (I$_A$) and (I$_B$).

A quite particular subject of the invention is, as medicaments, the products of formula (I$_C$) as defined above, said products of formula ($I_C$) being in all possible racemic or optically-active isomer forms, as well as the addition salts with pharmaceutically acceptable mineral and organic acids or mineral and organic bases of said products of formula (I).

An even more particular subject of the invention is, as medicaments, the products of formula ($I_D$) as defined above, said products of formula ($I_D$) being in all possible racemic or optically-active isomer forms, as well as the addition salts with pharmaceutically acceptable mineral and organic acids or mineral and organic bases of said products of formula (I).

A more particular subject of the invention is, as medicaments, the products described hereafter in the Examples and in particular the following products of formula (I):

1-((6-chloro-1,3-benzodioxol-5-yl) methyl)-4-(((4-methoxyphenyl) methyl) thio)-2-(phenylthio)-1H-imidazole-5-carboxaldehyde 4-bromo-1-((6-chloro-1,3-benzodioxol-5-yl) methyl)-2-phenyl-1H-imidazole-5-carboxylic acid 1-((6-chloro-1,3-benzodioxol-5-yl) methyl)-4-(((4-methoxyphenyl) methyl) thio)-2-(phenylthio)-1H-imidazole-5-carboxylic acid 1-((6-chloro-1,3-benzodioxol-5-yl) methyl)-4-(4-methoxyphenyl) thio)-2-(phenylthio)-1H-imidazole-5-carboxylic acid 1-((6-chloro-1,3-benzodioxol-5-yl) methyl)-2,4-bis(4-(methoxyphenyl) thio)-1H-imidazole-5-carboxylic acid 1-((6-chloro 1,3-benzodioxol-5-yl) methyl) 4-((3,4-dimethoxyphenyl) thio) 2-(1,3-dioxolan-2-yl) 1H-imidazol 5-carboxylic acid, as well as their addition salts with pharmaceutically acceptable mineral or organic acids or mineral and organic bases.

The medicaments, which are a subject of the invention, can be used, for example, in the treatment of any vascular spasms, in the treatment of post-cerebral haemorrhages, in the treatment of coronary spasms, peripheral vascular spasms as well as in the treatment of renal insufficiencies. These medicaments can also be used in the treatment of myocardial infarction, congestive cardiac insufficiency, in the prevention of post-angioplastic recurrence of stenosis, in the treatment of atherosclerosis and certain forms of hypertension such as in particular pulmonary hypertension, as well as in the treatment of asthma.

The medicaments, which are a subject of the invention, can also be used in the treatment of osteoporosis, prostatic hyperplasia and as neuronal protectors.

The invention extends to the pharmaceutical compositions containing at least one of the medicaments as defined above as active ingredient.

These pharmaceutical compositions can be administered by buccal, rectal route, by parenteral route or by local route as a topical application on the skin and mucous membranes or by injection by intravenous or intramuscular route.

These pharmaceutical compositions can be solid or liquid and be presented in the pharmaceutical forms currently used in human medicine, such as for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient treated and the illness in question, can be, for example, from 1 to 300 mg per day for an adult, by oral route or 1 to 100 mg per day by intravenous route.

Certain starting products of formulae (II) and (XVI) are known and can be prepared for example as indicated in the European Patent EP 0,168,950.

Other starting products of formulae (II) and (XVI) can in particular be prepared as indicated in the European Patent EP 0,465,368.

Certain starting products of formulae (II) and (XVI) are commercial products such as for example the following product of formula (II):
2-phenylimidazole from Aldrich.

Examples of commercial products of formula (XVI) are given in the Patents EP 0,465,368 or EP 0,503,162.

Certain products of formulae (II) and (XVI) can also be prepared in particular from products of formula (II) for example by subjecting them to one or more of the reactions described above in a) to u), carried out under the conditions also described above.

Certain products of formulae (XVI) can also be obtained by monohalogenation of the product of formula (II) as defined above into a product of formula ($P_1$):

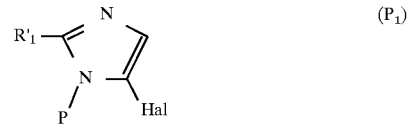

in which $R'_1$ and P have the meanings indicated above for the product of formula (II), which product of formula ($P_1$) can be reacted, after exchange following the metal halogen reaction known to a man skilled in the art, with the pertinent electrophilic compound, according to methods known to a man skilled in the art and in particular for example following the same type of reaction described above for passing for example from the compound of formula (XIII) to the compound of formula (XIV).

The starting compounds of formula (VIII) may be commercially-available such as 2,4,5-tribromoimidazole from Aldrich or can be prepared according to the usual methods known to a man skilled in the art.

The starting products of formulae ($V_a$), ($V_b$), ($VI_a$), ($VI_b$) and ($VI_c$) are commercial products such as in particular:
the following products of formula ($V_a$) or (XI):
  sec-butyl disulphide
  ethyl disulphide
  isopropyl disulphide
  methyl disulphide
  benzyl disulphide
  phenyl disulphide
  propyl disulphide
the following products of formula (Vb) or (XII):
  methyl methanethiosulphonate
  phenyl benzenethiol sulphonate
the following products of formula ($VI_a$):
  methyl chloroformate
  benzyl chloroformate
  isobutyl chloroformate
  ethyl chloroformate
  N-propyl chloroformate
the following products of formula ($VI_b$):
  dimethyl carbonate
  diethyl carbonate
the following products of formula ($VI_c$):

di-tert-butyl oxalate
diethyl oxalate
dimethyl oxalate

The starting products of formulae (X), (X') and (XII') are commercial products such as in particular:
the following products of formula (X):
benzaldehyde or butanal
the following products of formula (X'):
benzoyl or butyryl chloride
the following products of formula (XII'):
mesyl chloride
tosyl chloride A preparation process for some of the products of formula (III) is described in particular in the European Patent EP 0,465,368.

Examples of the preparation of compounds of formula (III) are also described in the literature and examples are given in particular in the U.S. Pat. No. 4,880,804 or for example in the reference Chemistry and Industry 7th Sep. 1987 HOWARD and COLQUHOUN pp. 612–617.

In particular, the product of formula (III) which is 6-chloro piperonyl chloride is commercially-available from Janssen.

Finally, a subject of the present invention is as new industrial products, the compounds of formulae (IV$_1$), (IV$_2$), (XIII), (XIV) and (XV) in which Y' represents the phenyl radical optionally substituted by one or more radicals chosen from halogen atoms and dioxol radicals, in which the optional reactive functions are optionally protected by protective groups.

Thus a particular subject of the invention is the use of the products of formula (I) as defined above, for the preparation of pharmaceutical compositions intended for the treatment of affections resulting from an abnormal stimulation of the endothelin receptors.

A more particular subject of the invention is the use of the products of formula (I) as defined above, for the preparation of pharmaceutical compositions intended for the treatment of hypertension induced by endothelin.

A quite particular subject of the invention is the use of the products of formula (I) as defined above, for the preparation of pharmaceutical compositions intended for the treatment of any vascular spasms and for the treatment of post-cerebral haemorrhages and renal insufficiencies.

Also a subject of the invention is the use of the products of formula (I) as defined above, for the preparation of pharmaceutical compositions intended for the treatment of myocardial infarction and for the prevention of post-angioplastic recurrence of stenosis.

The following examples illustrate the invention without however limiting it.

EXAMPLE 1

4-bromo-1-((6-chloro-1,3-benzodioxol-5-yl)methyl)-2-(phenylthio)-1H-imidazole-5-carboxaldehyde STAGE 1: 1-((6-chloro-1,3-benzodioxol-5-yl) methyl)-2,4,5-tribromo-1H-imidazole 25 g of 2,4,5 tribromoimidazole is introduced into 500 ml of dimethylformamide and 4.3 g of sodium hydride is added. Agitation is maintained for 10 minutes at ambient temperature. Next 18.4 g of 6 chloro piperonyl chloride, then 25 g of sodium iodide are added to the reaction medium and agitation is continued for 15 minutes at ambient temperature.

The reaction medium is finally poured into 3 l of water, followed by separating, washing abundantly with water, then successively with 250 ml of ethanol, 250 ml of isopropanol, then finally with 250 ml of isopropyl ether.

After drying, 31.5 g of expected product is collected (cream solid) M.p.=225° C.

IR CHCl$_3$ (cm$^{-1}$); Absence of =C—NH; Aromatic heterocycle 1624-1506-1497-1485

STAGE 2: 1-((6-chloro-1,3-benzodioxol-5-yl) methyl)-4,5-dibromo-2-(phenylthio)-1H-imidazole 4.73 g of the product obtained above in Stage 1 is introduced into 100 ml of a methylene chloride/sulphuric ether mixture (20/80), to which is added dropwise 3.5 ml of ethyl magnesium bromide: the reaction medium is maintained under agitation for 30 minutes at ambient temperature.

Then, 2.9 g of phenyl benzene thiosulphonate is introduced into the reaction medium obtained. Agitation is maintained for 2 hours at ambient temperature.

The medium is hydrolyzed by the addition of dilute hydrochloric acid, after extraction with ethyl acetate, washing abundantly with water then drying, a cream solid is obtained which is purified by impasting in 50 ml of ethanol. In this way 3.35 g of expected product is obtained.

M.p. 165° C.; IR CHCl$_3$ (cm$^{-1}$); Heterocycle+aromatic 1585-1508-1484; Microanalysis

|    | % calculated | % found |
|----|---|---|
| C  | 40.6 | 40.7 |
| H  | 2.2  | 2.1  |
| N  | 5.57 | 5.4  |
| S  | 6.37 | 6.4  |
| Br | 31.8 | 31.4 |
| Cl | 7.05 | 6.8  |

STAGE 3: 4-bromo-1-((6-chloro-1,3-benzodioxol-5-yl)methyl)-2-(phenylthio)-1H-imidazole-5-carboxaldehyde 6.4 g of the product obtained in Stage 2 above is introduced into 100 ml of tetrahydrofuran and 9.3 ml of ethyl magnesium bromide is added dropwise. The reaction medium is maintained under agitation for 30 minutes at ambient temperature.

Then, 5 equivalents of dimethyl formamide are introduced into the reaction medium obtained.

Agitation is maintained for 2 hours at ambient temperature.

The medium is hydrolyzed by the addition of dilute hydrochloric acid, after extraction with ethyl acetate, washing abundantly with water then drying, a brown solid is collected which is purified by chromatographing on silica with methylene chloride as eluant. 5 g of expected product is obtained (M.p.=155° C.) 500 mg of which is recrystallized from 25 ml of ethanol: after centrifuging then drying, 420 mg of expected product is obtained (white solid) (M.p.=155° C.).

IR CHCl$_3$ (cm$^{-1}$); C=O 1669; Aromatic+Heteroatom 1627-1580-1505-1485; Microanalysis

|    | % calculated | % found |
|----|---|---|
| C  | 47.9 | 47.9 |
| H  | 2.67 | 2.6  |
| N  | 6.2  | 6.1  |
| S  | 7.09 | 7.2  |
| Br | 17.68 | 17.7 |
| Cl | 7.84 | 7.7  |

EXAMPLE 2

1-((6-chloro-1,3-benzodioxol-5-yl) methyl)-4-(((4-methoxyphenyl) methyl) thio)-2-(phenylthio)-1H-imidazole-5-carboxaldehyde

620 mg of sodium hydride at 50% in oil is introduced into 50 ml of tetrahydrofuran, to which 1.8 ml of 4-methoxybenzenemethanethiol is added slowly. Agitation is maintained for 15 minutes at ambient temperature.

Then a solution of 3.8 g of the product of Example 1 in 25 ml of tetrahydrofuran is added to the thiolate thus formed. Agitation is continued under these conditions for 2 hours 30 minutes.

Finally, the reaction medium is poured into 0.1N soda, after extraction with ethyl acetate, washing abundantly with water then drying, a brown resin is collected which is purified by chromatographing on silica with methylene chloride 80/cyclohexane 20, then methylene chloride+20% ethyl acetate, as eluant.

2 fractions are collected, 1.97 g of the expected product (M.p.=135° C.) and 1.98 g of a second product which forms under the same operating conditions: 1-((6-chloro-1,3-benzodioxol-5-yl) methyl)-2,4-bis(((4-methoxyphenyl) methyl) thio)-1H-imidazole-5-carboxaldehyde.

CHECKS FOR A

IR $CHCl_3$ ($cm^{-1}$); C=O 1660; aromatic+Heterocycle 1611-1580-1513-1505-1485; Microanalysis

|   | % calculated | % found |
|---|---|---|
| C | 59.47 | 59.2 |
| H | 4.03 | 3.8 |
| N | 5.33 | 5.2 |
| S | 12.21 | 12.0 |
| Cl | 6.75 | 6.7 |

CHECKS FOR B

IR $CHCl_3$ ($cm^{-1}$); absence of phenyl S; C=O 1655; aromatic Heterocycle 1612-1585-1512-1508-1485

EXAMPLE 3

4-bromo-1-((6-chloro-1,3-benzodioxol-5-yl) methyl)-1H-imidazole-5-carboxaldehyde

STAGE 1: 1-((6-chloro-1,3-benzodioxol-5-yl) methyl)-4,5-dibromo-1H-imidazole

The operation is carried out as in Stage 2 of Example 1 starting with 6 g of the product obtained in Stage 1 of Example 1 in 300 ml of a methylene chloride/sulphuric ether mixture (60/240), to which 4.6 ml of ethyl magnesium bromide is added dropwise, then the whole is maintained under agitation for 30 minutes at ambient temperature and then 100 ml of ice-cooled water is introduced into the reaction medium obtained.

After acidification, extraction, washing then drying, 3.35 g of expected product is collected (homogeneous cream solid) (M.p. 150° C.).

IR $CHCl_3$ ($cm^{-1}$) Heterocycle+aromatic 1626-1508-1484

STAGE 2: 4-bromo-1-((6-chloro-1,3-benzodioxol-5-yl) methyl)-1H-imidazole-5-carboxaldehyde The operation is carried out as in Stage 3 of Example 1 starting with 900 mg of the product obtained in Stage 1 above in 10 ml of tetrahydrofuran and 1.7 ml of ethyl magnesium bromide is added dropwise. The reaction medium is maintained under agitation for 15 minutes at ambient temperature.

Then 0.9 ml i.e. 5 equivalents of dimethyl formamide are introduced into the reaction medium. Agitation is maintained for 2 hours at ambient temperature.

After hydrolysis of the medium by the addition of dilute hydrochloric acid, extraction, washing then drying, a cream solid is collected which is purified by chromatographing on silica with methylene chloride+5% of ethyl acetate as eluant. In this way 630 mg of expected product is obtained(M.p.=136° C.).

IR $CHCl_3$ ($cm^{-1}$; C=O 1670; Aromatic+Heteroatom 1625-1510-1485

EXAMPLE 4

1-((6-chloro-1,3-benzodioxol-5-yl) methyl)-4-(((4-methoxyphenyl) methyl) thio)-1H-imidazole-5-carboxaldehyde

The operation is carried out as in Example 2 starting with 90 mg of sodium hydride at 50% in oil in 10 ml of tetrahydrofuran, to which 0.26 ml of 4-methoxybenzenemethanethiol is added slowly.

Then a solution of 580 mg of the product of Example 3 in 5 ml of tetrahydrofuran is introduced into the thiolate thus formed and agitation is continued under these conditions for 2 hours 30 minutes. By proceeding as in Example 2, a brown resin is collected which is purified by chromatographing on silica with methylene chloride 95/ethyl acetate 5 as eluant and 400 mg of product is obtained which is purified by recrystallization from 20 ml of ethanol (M.p.=160° C.).

IR $CHCl_3$ ($cm^{-1}$); C=O 1664; aromatic+heterocycle 1610-1584-1513-1506-1483; Microanalysis

|   | % calculated | % found |
|---|---|---|
| C | 57.62 | 57.2 |
| H | 4.11 | 4.0 |
| N | 6.71 | 6.7 |
| S | 7.69 | 7.7 |
| Cl | 8.5 | 8.7 |

EXAMPLE 5

4-bromo-1-((6-chloro-1,3-benzodioxol-5-yl) methyl))-2-phenyl-1H-imidazole-5-carboxylic acid

STAGE 1: 1-((6-chloro-1,3-benzodioxol-5-yl) methyl)-2-phenyl-1H-imidazole 1.44 g of 2-phenyl imidazole is dissolved in 30 ml of dimethylformamide, 550 mg of sodium hydride at 50% in oil is added in small portions, the whole is left for 15 minutes at ambient temperature then 2.05 g of 6 chloro piperonyl chloride is added and the reaction medium is left overnight at ambient temperature. The dimethylformamide is evaporated off, 50 ml of saturated ammonium chloride is added and extraction is carried out with 3 times 70 ml of methylene chloride, followed by drying, evaporating and chromatographing on silica with ethyl acetate as eluant. In this way 2.8 g of expected product is obtained M.p.=163° C.

STAGE 2: 1-((6-chloro-1,3-benzodioxol-5-yl) methyl) 4,5-di-bromo-2-phenyl-1H-imidazole 2.8 g of the product obtained in Stage 1 above is dissolved in 50 ml of methylene chloride then 3.6 g of N-bromosuccinimide is added in small portions and the reaction medium is left overnight at ambient temperature. Then the organic phase is washed with N soda then with a saturated solution of sodium chloride, dried, evaporated and 3.3 g of expected product is collected after impasting in ether M.p.=173° C.

STAGE 3: 4-bromo-1-((6-chloro-1,3-benzodioxol-5-yl) methyl)-2-phenyl-1H-imidazole-5-carboxylic acid 750 ul of a 3M solution of ethyl magnesium bromide in ether is added dropwise, at ambient temperature, to a solution of 706 mg of the product obtained in Stage 2 above in 15 ml of anhydrous tetrahydrofuran, the reaction medium is left for 30 minutes at ambient temperature then an excess of $CO_2$ is bubbled through the solution for 30 minutes. Hydrolysis is carried out with saturated ammonium chloride followed by acidification to pH1 with 2N ethyl magnesium bromide and extraction is carried out with ethyl acetate. After drying and evaporating, the residue is recrystallized from methylene chloride in order to obtain 310 mg of expected product M.p.=215° C.

EXAMPLE 6

4-bromo 1-((6-chloro-1,3-benzodioxol-5-yl) methyl) -2-phenyl-1H-imidazole-5-carboxaldehyde 5.2 ml of 3M ethyl magnesium bromide in ether is added dropwise to a solution of 3.7 g of the product obtained in Stage 2 of Example 5 in 80 ml of anhydrous tetrahydrofuran, the reaction medium is left for 20 minutes at ambient temperature then 5 ml of anhydrous dimethylformamide is added and the whole is left for a further 2 hours at ambient temperature. Hydrolysis is carried out with saturated ammonium chloride and extraction is carried out with ethyl acetate. After drying and evaporating the solid residue is impasted in ether and 2.5 g of expected product is obtained M.p.=148° C.

EXAMPLE 7

1-((6-chloro-1,3-benzodioxol-5-yl) methyl)-4-(((4-methoxyphenyl) methyl) thio)-2-phenyl-1H-imidazole-5-carboxaldehyde The operation is carried out as in Example 2 starting with the product of Example 6.

250 mg of sodium hydride at 50% in oil is added to a solution of 635 ul of paramethoxybenzylthiol in 50 ml of dimethylformamide, the reaction medium is left for 15 minutes at ambient temperature and 1.7 g of the product of Example 6 is added then the whole is left for 4 hours at ambient temperature and the dimethylformamide is evaporated off. The residue is taken up in 1N soda and extraction is carried out with methylene chloride. The organic phase is dried, followed by evaporation and chromatography on silica with ethyl acetate/cyclohexane 2/8 as eluant. 1.31 g of expected product is obtained. M.p.=120° C.

EXAMPLE 8 methyl 1-((6-chloro-1,3-benzodioxol-5-yl) methyl)-4-(((4-methoxyphenyl) methyl) thio)-2-phenyl-1H-imidazole-5-carboxylate The operation is carried out as in Example 9 starting with the product of Example 7.

30 ml of methanol, 120 ul of acetic acid, 2.25 g of manganese oxide and 300 mg of sodium cyanide are added respectively to a solution of 600 mg of the product of Example 7 in methylene chloride. The reaction medium is left under agitation at ambient temperature for 96 hours, followed by filtering, washing with ethyl acetate and evaporating. 410 mg of expected product is obtained M.p.=158° C.

EXAMPLE 9 methyl 1-((6-chloro-1,3-benzodioxol-5-yl) methyl)-4-(((4-methoxyphenyl) methyl) thio)-2(phenylthio)-1H-imidazole-5-carboxylate 970 mg of the product of Example 2 is introduced into a mixture of methylene chloride/methanol (25 ml/100 ml) and then 5 g of manganese oxide, 500 mg of sodium cyanide and 200 ul of acetic acid are added successively. Agitation is then maintained for 72 hours at ambient temperature.

The reaction medium is separated, washed with methylene chloride then concentrated under vacuum.

The crude product is purified by rapidly passing it through silica with methylene chloride as eluant.

910 mg of crude expected product is obtained (M.p.=130° C.) which is recrystallized from 100 ml of ethanol. After separating , then drying, 815 mg of expected product is collected (white solid) (M.p.=130° C.).

IR $CHCl_3$ (cm$^{-1}$); ester 1699 1436; aromatic+heterocycle 1610-1584-1513-1505-1483; Microanalysis

|    | % calculated | % found |
|----|--------------|---------|
| C  | 58.4         | 58.5    |
| H  | 4.17         | 4.1     |
| N  | 5.04         | 4.9     |
| S  | 11.55        | 11.4    |
| Cl | 6.38         | 6.6     |

EXAMPLE 10

1-((6-chloro-1,3-benzodioxol-5-yl) methyl)-4-(((4-methoxyphenyl) methyl) thio)-2-(phenylthio)-1H-imidazole-5-carboxylic acid 500 mg of the product obtained in Example 9 is introduced into an ethanol/tetrahydrofuran mixture (15 ml/20 ml) and 15 ml of 2N soda is added. Agitation is maintained for 48 hours at ambient temperature.

The reaction medium is then acidified by the addition of 2N hydrochloric acid and after extraction with ethyl acetate, washing abundantly with water then drying, 340 mg of a cream residue is collected which is purified by chromatographing on silica with ethyl acetate 50/methylene chloride 50 as eluant.

Purification is carried out by recrystallization from 20 ml of ethanol and after separating then drying, 180 mg of expected product is collected (white solid) (M.p.=180° C.)

IR $CHCl_3$ (cm$^{-1}$); —OH 3510; —C=O 1704 1659; Conjugated system 1610-1580-1513-1505-1483; Microanalysis

|    | % calculated | % found |
|----|--------------|---------|
| C  | 57.7         | 57.5    |
| H  | 3.91         | 3.9     |
| N  | 5.18         | 5.2     |
| S  | 11.85        | 11.8    |
| Cl | 6.55         | 6.7     |

EXAMPLE 11 methyl 1-((6-chloro-1,3-benzodioxol-5-yl) methyl)-4-(((4-methoxyphenyl) methyl) thio)-1H-imidazole-5-carboxylate The operation is carried out as in Example 9 starting with 1 g of the product of Example 4 in a methylene chloride/methanol mixture (20 ml/50 ml) and then 6 g of manganese oxide, 750 mg of sodium cyanide and 400 ul of acetic acid are added successively. Agitation is then maintained for 48 hours at ambient temperature.

EXAMPLE 12

1-((6-chloro-1,3-benzodioxol-5-yl) methyl)-4-(((4-methoxyphenyl) methyl) thio)-1H-imidazole-5-carboxylic acid The operation is carried out as in Example 10 starting with 600 mg of the product of Example 11 in an ethanol/tetrahydrofuran mixture (25 ml/30 ml) and 50 ml of N soda is added.

Agitation is maintained for 48 hours at ambient temperature.

Proceeding as in Example 10, 310 mg of expected product is obtained in this way (M.p.=195° C.)

IR NUJOL (cm$^{-1}$); General absorption OH/NH; —C═O 1690; aromatic+heterocycle 1610-1583-1513-1508-1488; Microanalysis

|   | % calculated | % found |
|---|---|---|
| C | 55.5 | 55.4 |
| H | 3.95 | 3.7 |
| N | 6.47 | 6.5 |
| S | 7.4 | 7.3 |
| Cl | 8.2 | 8.2 |

EXAMPLE 13

1-((6-chloro-1,3-benzodioxol-5-yl)methyl)-4-(((4-methoxyphenyl)thio)-2-(phenylthio)-1H-imidazole-5-carboxaldehyde The operation is carried out as in Example 2 starting with 550 mg of sodium hydride at 50% in oil in 50 ml of tetrahydrofuran, then 1.4 ml of 4-methoxy-benzenethiol is added. Agitation is maintained for 15 minutes at ambient temperature.

Then a solution of 3.7 g of the product of Example 1 in 50 ml of tetrahydrofuran is introduced into the thiolate thus formed. Agitation is continued under these conditions for 1 hour 30 minutes.

Proceeding as in Example 2, 2 fractions are collected: 3.02 g of expected product and 600 mg of the product of Example 16.

IR CHCl$_3$ (cm$^{-1}$); C═O 1663; aromatic+heterocycle 1593-1580-1570-1505-1494-1484 of which S—o—OCH$_3$

EXAMPLE 14 methyl 1-((6-chloro-1,3-benzodioxol-5-yl) methyl)-4-(((4-methoxyphenyl) thio)-2-(phenylthio)-1H-imidazole-5-carboxylate The operation is carried out as in Example 9 starting with 1 g of the product of Example 13 in a methylene chloride/methanol mixture (20 ml/100 ml) and then 5 g of manganese oxide, 500 mg of sodium cyanide and 300 ul of acetic acid are added successively.

Agitation is then maintained for 24 hours at ambient temperature.

By proceeding as in Example 9, 820 mg of expected product is obtained (M.p.=140° C.).

IR CHCl$_3$ (cm$^{-1}$); ester 1704; aromatic+heterocycle 1593-1575-1505-1494-1483

EXAMPLE 15

1-((6-chloro-1,3-benzodioxol-5-yl)methyl)-4-(4-methoxyphenyl)thio)-2-(phenylthio)-1H-imidazole-5-carboxylic acid The operation is carried out as in Example 10 starting with 780 mg of the product of Example 14 in an ethanol/tetrahydrofuran mixture 20 ml/30 ml and 20 ml of N soda is added.

Agitation is maintained for 4 hours 30 minutes at ambient temperature.

Proceeding as in Example 10, 550 mg of expected product is obtained (M.p.=170° C.).

IR CHCl$_3$ (cm$^{-1}$); —OH/NH complex; C═O 1686; Aromatic+conjugated system 1592-1573-1503-1493; Microanalysis

|   | % calculated | % found |
|---|---|---|
| C | 57.0 | 56.8 |
| H | 3.63 | 3.4 |
| N | 5.3 | 5.3 |
| S | 12.16 | 11.8 |
| Cl | 6.72 | 6.8 |

EXAMPLE 16

1-((6-chloro-1,3-benzodioxol-5-yl)methyl)-2,4-bis(4-methoxyphenyl) thio))-1H-imidazole-5-carboxaldehyde The product of Example 16 (600 mg) is obtained during the preparation of Example 13 described above.

IR CHCl$_3$ (cm$^{-1}$); C═O 1663; Aromatic+heterocycle 1593-1575-1505-1495-1484 of which S—o—OCH$_3$

EXAMPLE 17 methyl 1-((6-chloro-1,3-benzodioxol-5-yl) methyl)-2,4-bis((4-methoxyphenyl) thio))-1H-imidazole-5-carboxylate The operation is carried out as in Example 9 starting with 470 mg of the product of Example 16 in a methylene chloride/methanol mixture 10 ml/50 ml and then 2.5 g of manganese oxide, 250 mg of sodium cyanide and 200 ul of acetic acid are added successively. Agitation is then maintained for 24 hours at ambient temperature.

Proceeding as in Example 9, 315 mg of expected product is obtained (M.p.=130° C.).

IR CHCl$_3$ (cm$^{-1}$); ester 1702; Aromatic+heterocycle 1593-1575-1505-1494-1483

EXAMPLE 18

1-((6-chloro-1,3-benzodioxol-5-yl)methyl)-2,4-bis(4-(methoxyphenyl)thio)-1H-imidazole-5-carboxylic acid The operation is carried out as in Example 10 starting with 280 mg of the product of Example 17 in an ethanol/tetrahydrofuran mixture 20 ml/20 ml, to which 20 ml of N soda is added. Agitation is maintained for 5 hours at ambient temperature.

Proceeding as in Example 10, 240 mg of expected product is obtained (M.p.=110° C.)

IR NUJOL (cm$^{-1}$); —C═O 1648; Aromatic+Heteroatom 1593-1573-1505-1489; Microanalysis

|    | % calculated | % found |
|----|--------------|---------|
| C  | 56.06        | 55.7    |
| H  | 3.8          | 3.8     |
| N  | 5.02         | 4.7     |
| S  | 11.5         | 11.2    |
| Cl | 6.36         | 6.5     |

EXAMPLE 19

1-((6-chloro-1,3-benzodioxol-5-yl)methyl)-5-(hydroxymethyl)-4-(4-(methoxyphenyl)thio)-2-(phenylthio)-1H-imidazole 820 mg of the product of Example 13 is introduced into 50 ml of ethanol and 60 mg of sodium borohydride is added.

Agitation is maintained for 30 minutes at ambient temperature.

0.5 ml of acetic acid then 50 ml of ice-cooled water are added.

After agitation for 10 minutes, the reaction medium is separated, washed with water, dried and 700 mg of crude product is collected which is purified by recrystallization from 20 ml of isopropanol, followed by separating and washing with 20 ml of ethanol.

410 mg of expected product is obtained (M.p.=146° C.)

IR CHCl$_3$ (cm$^{-1}$); —OH 3600+associated; Conjugated system 1627-1594-1583-1575-1505-1494-1484; Microanalysis

|    | % calculated | % found |
|----|--------------|---------|
| C  | 58.5         | 58.2    |
| H  | 4.13         | 4.0     |
| N  | 5.46         | 5.4     |
| Cl | 6.91         | 7.0     |
| S  | 12.5         | 12.3    |

EXAMPLE 20

1-((6-chloro-1,3-benzodioxol-5-yl)methyl)-4-((4-methoxyphenyl)thio)-2-phenyl-1H-imidazole-5-carboxaldehyde The operation is carried out as in Example 2 starting with 4 g of the product of Example 6 using 640 mg of sodium hydride at 50% in oil and 1.64 ml of 4-methoxy thiophenol and in this way 4.05 g of expected product is obtained. (M.p.=116° C.).

EXAMPLE 21 methyl 1-((6-chloro-1,3-benzodioxol-5-yl)methyl)-4-((4-methoxyphenyl)thio)-2-phenyl-1H-imidazole-5-carboxylate The operation is carried out as in Example 9 starting with 2 g of the product of Example 20 using 10 g of manganese oxide, 1 g of sodium cyanide, 200 ml of methanol, 40 ml of methylene chloride and 600 ul of acetic acid, in this way 1.64 g of expected product is obtained (M.p.=161° C.).

EXAMPLE 22

1-((6-chloro-1,3-benzodioxol-5-yl)methyl)-4-(4-methoxyphenyl)thio)-2-phenyl-1H-imidazole-5-carboxylic acid The operation is carried out as in Example 10 starting with 1 g of the product of Example 21 using 25 ml of 1N soda, 25 ml of ethanol and 50 ml of tetrahydrofuran. In this way 692 mg of expected product is obtained (M.p.=190° C.).

EXAMPLE 23 methyl 2-benzoyl-1-((6-chloro-1,3-benzodioxol-5-yl) methyl)-4-((4-methoxyphenyl)thio)-1H-imidazole-5-carboxylate STAGE 1: 1-((6-chloro-1,3-benzodioxol-5-yl)methyl)-4,5-dibromo-alpha-phenyl-1H-imidazole-2-methanol The operation is carried out as in Stage 2 of Example 1 starting with 9.5 g of the product obtained in Stage 1 of Example 1 in a mixture of methylene chloride/sulphuric ether 100 ml/350 ml and 7.3 ml of ethyl magnesium bromide is added dropwise. The reaction medium is maintained under agitation for 20 minutes at ambient temperature.

Then 10 ml of benzaldehyde is introduced into the reaction medium.

Agitation is maintained for 2 hours at ambient temperature.

Proceeding as in Stage 2 of Example 1, 5.34 g of expected product is obtained.

IR CHCl$_3$ (cm$^{-1}$); —OH 3603+general absorption; Aromatic heteroatom 1627-1603-1505-1484

STAGE 2: 4-bromo-1-((6-chloro-1,3-benzodioxol-5-yl)methyl)-2-(alpha-hydroxy-(phenylmethyl))-1H-imidazole-5-carboxaldehyde The operation is carried out as in Stage 3 of Example 1 starting with 5.3 g of the product obtained in Stage 1 above in 100 ml of tetrahydrofuran and 11 ml of ethyl magnesium bromide is added dropwise. The reaction medium is maintained under agitation for 15 minutes at ambient temperature.

Then 5 ml of dimethylformamide is introduced into the reaction medium. Agitation is maintained for 2 hours at ambient temperature.

Proceeding as in Stage 3 of Example 1, 2.067 g of expected product is obtained.

IR CHCl$_3$ (cm$^{-1}$); C═O 1674; —OH complex 3596; Aromatic+heterocycle 1628-1602-1505-1485

STAGE 3: 1-((6-chloro-1,3-benzodioxol-5-yl) methyl)-2-(alpha-hydroxy-(phenylmethyl))-4-((4-methoxyphenyl)thio)-1H-imidazole-5-carboxaldehyde The operation is carried out as in Example 2 starting with a suspension of 390 mg of sodium hydride at 50% in oil in 50 ml of tetrahydrofuran, to which 1 ml of 4-methoxy-benzenethiol is added slowly. Agitation is maintained for 15 minutes at ambient temperature.

Then a solution of 2.6 g of the product obtained in Stage 2 above in 25 ml of tetrahydrofuran is added to the thiolate thus formed. Agitation is continued under these conditions for 2 hours.

Proceeding as in Example 2, 2.15 g of expected product is obtained.

IR CHCl$_3$ (cm$^{-1}$); C═O 1667; —OH 3598 associated; aromatic+heterocycle 1593-1574-1505-1494-1484

STAGE 4: methyl 2-benzoyl-1-((6-chloro-1,3-benzodioxol-5-yl)methyl)-4-((4-methoxyphenyl)thio)-1H-imidazole-5-carboxylate The operation is carried out as in Example 9 starting with 2.15 g of the product obtained in Stage 3 above in 200 ml of methanol, then 11 g of manganese oxide, 1.1 g of sodium cyanide and 700 ul of acetic acid are added successively.

Agitation is then maintained for 48 hours at ambient temperature.

Proceeding as in Example 9, 1.32 g of expected product is obtained (M.p.=166° C.).

IR CHCl$_3$ (cm$^{-1}$); Absence of OH; C=O 1716-1653; Aromatic+heterocycle 1597-1579-1508-1495

EXAMPLE 24

2-benzoyl-1-((6-chloro-1,3-benzodioxol-5-yl) methyl)-4-((4-methoxyphenyl)thio-1H-imidazole-5-carboxylic acid The operation is carried out as in Example 10 starting with 400 mg of the product of Example 23 in an ethanol/tetrahydrofuran mixture 30 ml/30 ml and 10 ml of N soda is added.

Agitation is maintained for 48 hours at ambient temperature.

Proceeding as in Example 10, 385 mg of expected product is obtained (M.p.=210° C.).

IR NUJOL (cm$^{-1}$); General absorption OH/NH; —C=O 1679-1652; Aromatic+heterocycle 1590-1572-1503-1485; Microanalysis

|    | % calculated | % found |
|----|--------------|---------|
| C  | 59.71        | 59.4    |
| H  | 3.66         | 3.7     |
| N  | 5.35         | 5.2     |
| S  | 6.13         | 6.0     |
| Cl | 6.77         | 7.0     |

EXAMPLE 25

1-((6-chloro-1,3-benzodioxol-5-yl)methyl)-4-(((4-methoxyphenyl)methyl)thio)-2-phenyl-1H-imidazole-5-carboxylic acid The operation is carried out as in Example 10 starting with the product of Example 8.

30 ml of 2N soda is added to a solution of 740 mg of the product of Example 8 in a tetrahydrofuran/ethyl acetate mixture (50 ml/50 ml) and the reaction medium is left for 96 hours to ambient temperature, followed by evaporating, taking up in 30 ml of water, acidifying with 1N hydrochloric acid and filtering.

In this way 440 mg of expected product is obtained (M.p.=190° C.).

EXAMPLE 26

1-((6-chloro 1,3-benzodioxol-5-yl) methyl)-4-((3,4-dimethoxyphenyl) thio-2-dioxolan-2-yl) 1H-imidazol-5-carboxaldehyde STAGE A: 1-((6-chloro 1,3-benzodioxol-5-yl) methyl) 4,5-di-bromo 2-(1,3-dioxolan-2-yl) 1H-imidazole.

15.6 ml of a 3M solution of ethyl magnesium bromide in ether is added to 20 g of product obtained as in Example 1 Stage A in 200 ml of dichloromethane and 500 ml of ether and the whole is agitated for 20 minutes at ambient temperature. 200 ml of N hydrochloric acid is added and extraction is carried out with ethyl acetate. The organic phase is washed with water, dried and the solvent is evaporated off. The intermediate aldehyde obtained is taken up in 200 ml of toluene, 20 ml of ethylene glycol is added and heating under reflux is carried out for 16 hours. The solvent is evaporated off, the residue is taken up in a saturated aqueous solution of sodium bicarbonate, extraction is carried out with ethyl acetate, followed by washing with water, drying, and the solvent is evaporated off under reduced pressure. The residue is impasted in isopropyl ether, followed by filtration and drying under reduced pressure and 13.5 g of expected product is collected. M.p.=188° C.

STAGE B: 4-bromo 1-((6-chloro 1,3-benzodioxol-5-yl) methyl) 2-(1,3-dioxolan-2-yl) 1H-imidazol 5-carboxaldehyde.

10 g of the product obtained in Stage A above is introduced into 200 ml of tetrahydrofuran and 10 ml of ethyl magnesium bromide in a 3M solution in ether is added dropwise. The reaction medium is maintained under agitation for 20 minutes at ambient temperature. 10 ml of dimethylformamide is then added to the reaction medium obtained and agitation is carried out for 2 hours at ambient temperature. The medium is hydrolyzed by the addition of 200 ml of dilute hydrochloric acid, extraction is carried out with ethyl acetate, followed by washing with water then drying and after impasting in isopropyl ether, 7.6 g of expected product is recovered, which is used as it is for the following stage.

STAGE C: 1-((6-chloro 1,3-benzodioxol-5-yl) methyl) 4-( (3,4-dimethoxyphenyl) thio-2-dioxolan-2-yl) 1H-imidazol-5-carboxaldehyde.

1.1 g of sodium hydride is added to 3.15 ml of 3,4-dimethoxythiophenol in solution in 200 ml of dimethylformamide and the whole is agitated for 20 minutes at ambient temperature. 7.6 g of the product obtained in Stage B is added, agitation is continued for 16 hours at ambient temperature, the solvent is evaporated under reduced pressure, the residue is taken up in 200 ml of a saturated aqueous solution of ammonium chloride and extraction is carried out with dichloromethane. The organic phase is dried, the solvent is evaporated off, the residue is impasted in isopropyl ether, filtration is carried out and 5.2 g of expected product is obtained. M.p.=149° C.

EXAMPLE 27 methyl 1-((6-chloro 1,3-benzodioxol-5-yl) methyl) 4-((3,4-dimethoxyphenyl) thio-2-dioxolan-2-yl) 1H-imidazol-5-carboxylate A solution of 5.05 g of the product of Example 26 is introduced into a mixture of methylene chloride/methanol (100 ml/500 ml), next 22 g of manganese oxide, 2.2 g of sodium cyanide and 1.5 ml of acetic acid are successively added then the whole is agitated for 72 hours at ambient temperature. After filtration, the organic phase is washed with water, dried, the solvent is evaporated off and after chromatography on silica 4.1 g of expected product is obtained. M.p.=170° C.

EXAMPLE 28

1-((6-chloro 1,3-benzodioxol-5-yl) methyl) 4-((3,4-dimethoxyphenyl) thio-2-(1,3-dioxolan-2-yl) 1H-imidazol-5-carboxylic acid 1 g of the product obtained in Example 27 is introduced into 100 ml of ethanol and 50 ml of 2N soda is added.

Agitation is carried out for 16 hours at ambient temperature, the solvent is evaporated off under reduced pressure, the residue is taken up in a mixture of ice-cooled water, acidified with 2N hydrochloric acid, extraction is carried out with ethyl acetate, followed by drying and the solvent is evaporated off under reduced pressure. 650 mg of expected product is recovered. M.p.=155° C.

EXAMPLE 29 of pharmaceutical composition

Tablets were prepared corresponding to the following formula:
Product of Example 10 . . . 50 mg
Excipient for a tablet completed at . . . 200 mg
(detail of excipient: lactose, talc, starch, magnesium stearate).

PHARMACOLOGICAL RESULTS

STUDY OF THE ACTIVITY ON THE B RECEPTOR OF ENDOTHELIN

A membrane preparation is produced from the posterior cortex plus cerebellum of a rat. The tissue is ground up in a POLYTRON in a 50 mM Tris buffer pH=7.4.

After 30 minutes at 25° C. (W.B.) the homogenate is centrifuged at 30000 g for 15 minutes (2 centrifugations with intermediate take-up in the Tris buffer pH. 7.4).

The pellets are resuspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquots are distributed into hemolysis tubes and $^{125}$I Endothelin (approximately 50000 dpm/tube) and the product to be studied are added. (The product is first tested at $3 \times 10^{-5}$M three times). When the tested product displaces more than 50% of the radioactivity specifically bound to the receptor, it is tested again according to a range of 7 concentrations so as to determine the concentration which inhibits the radioactivity specifically bound to the receptor by 50%. In this way the 50% inhibitory concentration is determined.

The non-specific bond is determined by the addition of $10^{-6}$M endothelin (three times). After incubation at 25° C. for 60 minutes, putting back in the water bath at 0° C., for 5 minutes, filtering under reduced pressure, rinsing with Tris buffer 7.4, the radioactivity is counted in the presence of scintillating Triton.

The result is expressed directly as the 50% inhibitory concentration (IC50), that is to say as the concentration of product studied expressed in nM, necessary to displace 50% of the specific radioactivity bound to the receptor studied.
Result:

The IC50's found for the products of the Examples are given in Table I hereafter, in nanomoles.
Results:

TABLE I

| Product of Examples | B receptor of endothelin IC50 in nanomoles |
| --- | --- |
| 10 | 420 |
| 15 | 110 |
| 18 | 88 |

STUDY OF THE ACTIVITY ON THE A RECEPTOR OF ENDOTHELIN

A membrane preparation is produced from the heart (ventricles) of a rat. The tissue is ground up in a POLYTRON in a 50 mM Tris buffer pH=7.4.

After 30 minutes at 25° C. (W.B.) the homogenate is centrifuged at 30000 g for 15 minutes (2 centrifugations with intermediate take up in the Tris buffer pH. 7.4).

The pellets are resuspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquots are distributed into hemolysis tubes and $^{125}$I Endothelin (approximately 50000 dpm/tube) and the product to be studied are added. (The product is first tested at $3 \times 10^{-5}$M three times). When the tested product displaces more than 50% of the radioactivity specifically bound to the receptor, it is tested again according to a range of 7 concentrations so as to determine the concentration which inhibits the radioactivity specifically bound to the receptor by 50%. In this way the 50% inhibitory concentration is determined.

The non-specific bond is determined by the addition of $10^{-6}$M endothelin (three times). After incubation at 25° C. for 60 minutes, putting back in the water bath at 0° C., for 5 minutes, filtering under reduced pressure, rinsing with Tris buffer 7.4, the radioactivity is counted in the presence of scintillating Triton.

The result is expressed directly as the 50% inhibitory concentration (IC50), that is to say as the concentration of product studied expressed in nM, necessary to displace 50% of the specific radioactivity bound to the receptor studied.
Result:

The IC50's found for the products of the Examples are given in Table II hereafter, in nanomoles.
Results:

TABLE II

| Product of Examples | B receptor of endothelin IC50 in nanomoles |
| --- | --- |
| 10 | 167 |
| 15 | 170 |
| 18 | 230 |

We claim:

1. A compound selected from the group consisting of a compound in all possible racemic, enantiomeric and diastereomeric forms selected from the group consisting of a compound of the formula

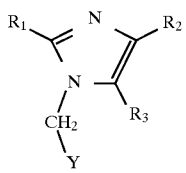

wherein $R_1$ is selected from the group consisting of hydroxyl, formyl, dioxol, aryl, aryl carbonyl, arylthio, alkoxy and alkyl carbonyl with alkyl of 1 to 6 carbon atoms, the aryl and alkyl unsubstituted or substituted with at least one member selected from the group consisting of —OH, carboxy, carboxy esterified with an alkanol of 1 to 6 carbon atoms, —CONH$_2$, carboxy salified with a base, —CN, —NO$_2$, —NH$_2$, mono and di-alkylamino of 1 to 6 alkyl carbon atoms, cycloalkyl of 3 to 7 carbon atoms, alkyl and alkoxy of 1 to 6 carbon atoms, alkenyl of 2 to 6 carbon atoms, haloalkyl, alkoxythio, haloalkylthio and haloalkoxy of 1 to 6 carbon atoms, phenoxy, phenyl alkoxy of 1 to 6 alkyl carbon atoms, carbamoyl, acyl and acyloxy of an organic carboxylic acid of 1 to 6 carbon atoms, tetrazolyl, tetrazolyl salified with a base and phenyl unsubstituted or substituted with at least one member of the group consisting of halogen, —OH, alkyl and alkoxy of 1 to 4 carbon atoms, —CF$_3$, —CN, carboxy, carboxy esterified with alkanol of 1 to 6 carbon atoms, carboxy salified with a base and tetrazolyl, $R_2$ and $R_3$ are individually selected from the group consisting of a) halogen, —SH, acyl of an organic carboxylic acid of 1 to 6 carbon atoms, carboxy, —CONH$_2$, carboxy salified with a base, carboxy esterified with an alkanol of 1 to 6 carbon atoms, —NO$_2$, —CN and —P(O)(OR)$_2$ and R is selected from the group consisting of hydrogen, alkyl of 1 to 4 carbon atoms and phenyl, b) $R_4$ and —OR$_4$ wherein $R_4$ is —(CH$_2$)$_{m1}$—S(O)$_{m2}$—X—R$_{10}$ wherein m1 is an integer from 0 to 4, m2 is an integer from 0 to 2 and —XR$_{10}$ is amino or X is selected from the group consisting of a single bond, —NR$_{11}$—, —NR$_{11}$—CO—, —NR$_{11}$COO—, —NR$_{11}$—CONR$_{12}$— and —N=CR$_{11}$—NR$_{12}$, $R_{10}$ is selected from the group consisting of alkyl and alkenyl of up to 6 carbon atoms and aryl, all unsubstituted or substituted with at least one member of the group consisting of a') —OH, halogen, cycloalkyl of 3 to 7 carbon atoms, b') alkyl, alkoxy, haloalkyl, alkylthio, haloalkylthio and haloalkoxy of 1 to 6 carbon atoms, c') phenoxy, phenylalkoxy of 1 to 6 alkyl carbon atoms, carbamoyl, acyl and acyloxy of an organic carboxylic acid of 1 to 6 carbon atoms, carboxy, carboxy salified with a base, carboxy esterified with an alkanol of 1 to 6 carbon atoms, tetrazolyl, —CN, —NO$_2$, —NH$_2$, mono and dialkylamino of 1 to 6 alkyl carbon atoms and aryl substituted with at least one member of the group consisting of halogen, —OH, alkyl and alkoxy of 1 to 4 carbon atoms, —CF$_3$, tetrazolyl, carboxy, carboxy salified with a base and carboxy esterified with an alkanol of 1 to 6 carbon atoms and $R_{11}$ and $R_{12}$ are individually hydrogen or a value of $R_{10}$ or $R_4$ is selected from the group consisting of a) hydrogen, b) alkyl, alkenyl, alkynyl and acyl of an organic carboxylic acid, all up to 6 carbon atoms and uninterrupted or interrupted by at least of one heteroatom selected from the group consisting of oxygen, sulfur and nitrogen, c) amino and carbamoyl unsubstituted or substituted with 1 to 2 alkyl and alkynyl of up to 6 carbon atoms, d) —(CH$_2$)$_{m1}$—S(O)$_{m2}$—XR$_{10}$ as defined above and e) cycloalkyl of 3 to 6 carbon atoms and aryl with the alkyl, alkenyl and aryl of $R_4$ being unsubstituted or substituted by at least one member of the group consisting of a) halogen, —OH, —SH, —CN, azido, —NO$_2$, —SO$_3$H, carboxy, carboxy salified with a base, carboxyl esterified with an alkanol of 1 to 6 carbon atoms and amidified carboxy, b) alkyl, alkenyl, alkoxy, haloalkyl, alkylthio, alkenylthio, alkynylthio, haloalkylthio, haloalkoxy, and acyl, acylthio and acyloxy of an organic carboxylic acid, all of up to 6 carbon atoms, c) aryl, arylthio, aralkyl, aralkenyl, aryloxy and arylalkoxy wherein the aryl is unsubstituted or substituted by at least one member of the group consisting of halogen, —OH, alkyl and alkoxy of 1 to 6 carbon atoms, haloalkyl, alkylthio, haloalkylthio, haloalkoxy, carbamoyl, acyl and acyloxy of an organic carboxylic acid of 1 to 6 carbon atoms, carboxy, carboxy salified with a base, carboxy esterified with an alkanol of 1 to 6 carbon atoms, —CN, —NO$_2$, —NH$_2$, mono and dialkylamino of 1 to 6 alkyl carbon atoms, tetrazolyl and phenyl unsubstituted or substituted with at least one member of the group consisting of halogen, —OH, alkyl and alkoxy of 1 to 4 carbon atoms, —CF$_3$, tetrazolyl, carboxy, carboxy salified with a base and carboxy esterified with an alkanol of 1 to 6 carbon atoms and f)

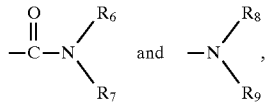

wherein $R_6$ and $R_7$ and $R_8$ and $R_9$ are individually selected from the group consisting of a) hydrogen, amino acids, b) alkyl and alkenyl of up to 6 carbon atoms unsubstituted or substituted by at least one member of the group consisting of halogen, —OH and alkoxy of 1 to 6 carbon atoms, c) aryl, aralkyl and arylalkenyl of up to 6 alkyl carbon atoms, all unsubstituted or substituted by at least one member of the group consisting of halogen, —OH, —CN, —NO$_2$, alkyl, alkenyl, haloalkyl, alkoxy and acyl of an organic carboxylic acid, all of up to 6 carbon atoms, —NH$_2$, mono and dialkylamino of 1 to 6 carbon atoms, carboxy, salified carboxy and carboxy esterified with an alkanol of 1 to 6 carbon atoms and aryl and aralkyl optionally substituted with at least one member of the group consisting of halogen, —OH, —CF$_3$, —NO$_2$, —CN, tetrazolyl, carboxy, carboxy salified with a base and carboxy esterified with an alkanol of 1 to 6 carbon atoms and d) —(CH$_2$)$_{m1}$—S(O)$_{m2}$—XR$_{10}$ defined as above or $R_6$ and $R_7$ or $R_8$ and $R_9$ together with the nitrogen to which they are attached form a heterocycle selected from the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepine, indolyl, unsubstituted or substituted by at least by one member of the group consisting of halogen, hydroxyl, nitro, cyano, acyl, trifluoromethyl, alkyl and alkoxy of 1 to 4 carbon atoms, free carboxy, salified carboxy, esterified carboxy, amidified carboxy, tetrazolyl, oxazolyl and phenyl, or $R_8$ and $R_9$ are individually acyl of an organic carboxylic acid of 1 to 6 carbon atoms or one of $R_8$ and $R_9$ is carbamoyl or alkoxy carbonyl or benzyloxycarboxyl and the other is $R_8$ as defined above or $R_8$ and $R_9$ together with the nitrogen atom form phthalimido or succinimido, Y is —Y$_1$—B—Y$_2$, $Y_1$ is aryl unsubstituted or substituted with dioxol or one of $R_2$ and $R_3$, B is a single bond or a member of the group consisting of

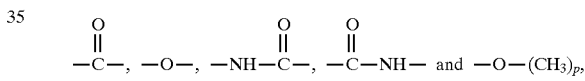

p is 1, 2 or 3, $Y_2$ is $Y_1$, whatever B is or when B is a single bond, $Y_2$ is selected from the group consisting of hydrogen, alkoxy of 1 to 6 carbon atoms, halogen, —CN, tetrazolyl, carboxy, carboxy salified with a base, carboxy amidified, carboxy esterified with an alkanol or 1 to 6 carbon atoms and —(CH$_2$)$_{m1}$—S(O)$_{m2}$—XR$_{10}$ defined as above and their non-toxic, pharmaceutically acceptable acid addition salts.

2. A compound of claim 1 wherein Y is selected from the group consisting of phenyl unsubstituted or substituted with at least one halogen or dioxol and at least one $R_{2B}$ and $R_{3B}$ is selected from the group consisting of —(CH$_2$)$_{m3}$—S(O)$_{m2}$—X$_B$—R$_{10B}$ as defined in claim 1, alkyl substituted with a member of the group consisting of carboxy, carboxy salified with a base, carboxy esterified with an alkanol of 1 to 6 carbon atoms and —CONH$_2$, formyl, aryl, carboxy, carboxy salified with a base, carboxy esterified with an alkanol of 1 to 6 carbon atoms and —CONH$_2$.

3. A compound of claim 1 wherein $R_1$ is selected from the group consisting of hydrogen, alkoxy of 1 to 6 carbon atoms, dioxol, phenyl benzoyl and phenylthio, the phenyls being unsubstituted or substituted with —OH or alkoxy of 1 to 4 carbon atoms, $R_2$ and $R_3$ are individually selected from the group consisting of halogen, carboxy, carboxy salified with a base, carboxy esterified with an alkanol of 1 to 4 carbon atoms, formyl, tetrazolyl, phenyl, phenylthio, phenyl sulfonyl, phenyl sulfinyl and alkyl, alkylthio, alkyl sulfonyl and alkyl sulfinyl of 1 to 4 carbon atoms; all unsubstituted or substituted with at least one member of the group consisting of halogen, —OH, alkoxy of 1 to 4 carbon atoms, carboxy, carboxy salified with a base, carboxy esterified with an alkanol of 1 to 4 carbon atoms and phenyl unsubstituted or substituted with —OH or alkoxy of 1 to 4 carbon atoms and Y is phenyl unsubstituted or substituted with dioxol and at least one halogen.

4. A compound of claim 1 wherein $R_1$ is selected from the group consisting of hydrogen, 1,3-dioxolane, phenyl, benzoyl and phenylthio, the phenyls unsubstituted or substituted with —OH or alkoxy of 1 to 4 carbon atoms, $R_2$ is selected from the group consisting of halogen, alkylthio of 1 to 4 carbon atoms optionally substituted by phenyl unsubstituted or substituted with alkoxy of 1 to 4 carbon atoms and phenylthio unsubstituted or substituted with alkoxy of 1 to 4 carbon atoms, $R_3$ is selected from the group consisting of formyl, carboxy, carboxy salified with a base, carboxy esterified with an alkanol of 1 to 4 carbon atoms and —$CONH_2$ and Y is phenyl substituted with halogen and dioxol.

5. A compound of claim 1 selected from the group consisting of 1-((6-chloro-1,3-benzodioxol-5-yl)-methyl)-4-(4-methoxy-benzylthio)-2-(phenylthio)-1H-imidazole-5-carboxaldehyde, 4-bromo-1-((6-chloro-1,3-benzodioxol-5-yl)-methyl)-2-phenyl-1H-imidazole-5-carboxylic acid, 1-((6-chloro-1,3-benzodioxol-5-yl-methyl)-4-(4-methoxybenzylthio)-2-(phenylthio)-1H-imidazole-5-carboxylic acid, 1-((6-chloro-1,3-benzodioxol-5-yl)-methyl-4-(4-methoxy-thio)-2-(phenylthio)-1H-imidazole-5-carboxylic acid, 1-((6-chloro-1,3-benzodioxol-5-yl)-methyl-2,4-bis(4-(methoxyphenyl)-thio)-1H-imidazole-5-carboxylic acid and 1-((6-chloro-1,3-benzodioxol-5-yl)-methyl)-4-((3,4-dimethoxyphenyl)-thio)-2-(1,3-dioxolan-2-yl)-1H-imidazol-5-carboxylic acid.

6. A composition for treating conditions resulting from abnormal stimulation of endothelin receptors comprising an inhibitorily effective amount to prevent abnormal stimulation of endothelin receptors of a compound of claim 1 and a non-toxic, pharmaceutical carrier.

7. A composition for treating conditions resulting from abnormal stimulation of endothelin receptors comprising an inhibitorily effective amount to prevent abnormal stimulation of endothelin receptors of a compound of claim 2 and a non-toxic, pharmaceutical carrier.

8. A composition for treating conditions resulting from abnormal stimulation of endothelin receptors comprising an inhibitorily effective amount to prevent abnormal stimulation of endothelin receptors of a compound of claim 1 and a non-toxic, pharmaceutical carrier.

9. A method of preventing abnormal stimulation of endothelin receptors in human beings comprising administering to warm-blooded animals an amount of a compound of claim 1 sufficient to prevent said abnormal stimulation.

10. A method of treating hypertension induced by endothelin in warm-blooded animals comprising administering to warm-blooded animals a sufficient amount of a compound of claim 1 to prevent abnormal stimulation of endothelin receptors.

* * * * *